US012742172B2

(12) United States Patent
Zhang et al.

(10) Patent No.: US 12,742,172 B2
(45) **Date of Patent: *Sep. 22, 2026**

(54) ENGINEERED DNA MOLECULE FOR CODING RNA

(71) Applicants: RINUAGENE BIOTECHNOLOGY CO., LTD., Jiangsu (CN); RINUAGENE INTERNATIONAL HK LIMITED, Kowloon (CN)

(72) Inventors: Weiguo Zhang, Suzhou (CN); Yijie Dong, Suzhou (CN); Hua Chen, Suzhou (CN); Wei Qin, Suzhou (CN)

(73) Assignees: RINUAGENE BIOTECHNOLOGY CO., LTD., Suzhou (CN); RINUAGENE INTERNATIONAL HK LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/083,930

(22) Filed: Mar. 19, 2025

(65) Prior Publication Data

US 2025/0215441 A1 Jul. 3, 2025

Related U.S. Application Data

(63) Continuation of application No. PCT/CN2024/079346, filed on Feb. 29, 2024.

(30) Foreign Application Priority Data

Mar. 1, 2023 (WO) ................ PCT/CN2023/079037
Feb. 23, 2024 (CN) ......................... 202410205083.1

(51) Int. Cl.

*C12N 15/68* (2006.01)
*C07K 14/005* (2006.01)
*C12N 1/20* (2026.01)
*C40B 40/08* (2006.01)
*C12R 1/185* (2006.01)

(52) U.S. Cl.

CPC ............ *C12N 15/68* (2013.01); *C07K 14/005* (2013.01); *C12N 1/20* (2013.01); *C40B 40/08* (2013.01); *C12N 2710/20022* (2013.01); *C12N 2830/50* (2013.01); *C12R 2001/185* (2021.05)

(58) Field of Classification Search

None
See application file for complete search history.

(56) References Cited

U.S. PATENT DOCUMENTS

| | | | | |
|---|---|---|---|---|
| 12,315,441 | B2 * | 5/2025 | Choi | G09G 3/3233 |
| 2017/0166905 | A1 * | 6/2017 | Eberle | C12N 15/70 |
| 2017/0304385 | A1 * | 10/2017 | Jin | A61K 38/02 |
| 2023/0310655 | A1 * | 10/2023 | Yu | C12N 9/0069 514/44 R |
| 2025/0222094 | A1 * | 7/2025 | Cen | C07K 16/2827 |

FOREIGN PATENT DOCUMENTS

| | | | |
|---|---|---|---|
| CN | 107073070 | A | 8/2017 |
| CN | 111212908 | A | 5/2020 |
| CN | 112805386 | A | 5/2021 |
| CN | 113088519 | A | 7/2021 |
| CN | 115698303 | A | 2/2023 |
| EP | 4 123 029 | A1 | 1/2023 |
| EP | 4 389 901 | A1 | 6/2024 |
| WO | 2013/090648 | A1 | 6/2013 |
| WO | 2014/152211 | A1 | 9/2014 |
| WO | 2015/038892 | A1 | 3/2015 |
| WO | 2015/164674 | A1 | 10/2015 |
| WO | 2016/024255 | A1 | 2/2016 |
| WO | 2016/118724 | A1 | 7/2016 |
| WO | 2017/031232 | A1 | 2/2017 |
| WO | 2017/049074 | A1 | 3/2017 |
| WO | 2017/049245 | A2 | 3/2017 |
| WO | 2017/075531 | A1 | 5/2017 |
| WO | 2017/099823 | A1 | 6/2017 |
| WO | 2017/112865 | A1 | 6/2017 |
| WO | 2017/117528 | A1 | 7/2017 |
| WO | 2017/180917 | A2 | 10/2017 |
| WO | 2017/218704 | A1 | 12/2017 |
| WO | 2017/223135 | A1 | 12/2017 |
| WO | 2019/036513 | A1 | 2/2019 |
| WO | 2020/074642 | A1 | 4/2020 |
| WO | 2022028559 | A1 | 2/2022 |
| WO | 2023/022490 | A1 | 2/2023 |
| WO | 2024/041641 | A1 | 2/2024 |

OTHER PUBLICATIONS

Liu, Man, Xiaohui Wu, and Qingshun Quinn Li. "DNA/RNA hybrid primer mediated poly (A) tag library construction for Illumina sequencing." Polyadenylation in Plants: Methods and Protocols. New York, NY: Springer New York, 2014. 175-184. (Year: 2014).*
Chen et al., "Poly(A) variants supporting robust transmission stability in bacteria and high protein expression in animals for mRNA vitro transcription," Molecular Therapy-Nucleic Acids, vol. 37, No. 1, Mar. 1, 2026 (Mar. 1, 2026), p. 102809, XP093403803.
Trepotec et al., "Segmented poly(A) tails significantly reduce recombination of plasmid DNA without affecting mRNA translation efficiency or half-life," RNA 25(4): 507-518 (2019).
Lim et al., "Mixed tailing by TENT4A and TENT4B shields mRNA from rapid deadenylation," Science 361(6403): 701-704 (2018).

* cited by examiner

*Primary Examiner* — Brian Whiteman
*Assistant Examiner* — Khaleda B Hasan
(74) *Attorney, Agent, or Firm* — Leydig, Voit & Mayer, Ltd.

(57) ABSTRACT

An engineered DNA molecule capable of being replicated in a cell, comprising a poly (A) tail coding sequence that makes the engineered DNA molecule more conservative when replicated in cells, particularly in prokaryotic cells, while adjusting the expression level of RNA in eukaryotic cells. Also provided are an RNA comprising the poly (A) tail and a use thereof.

25 Claims, 4 Drawing Sheets

Specification includes a Sequence Listing.

(ns, no significant difference; **, significant difference, p<0.01)

ENGINEERED DNA MOLECULE FOR CODING RNA

CROSS-REFERENCE TO RELATED APPLICATIONS

This patent application is a continuation of co-pending International Application No. PCT/CN2024/079346, filed Feb. 29, 2024, which claims priority to Chinese Patent Application No. 202410205083.1, filed Feb. 23, 2024; and International Application No. PCT/CN2023/079037, filed Mar. 1, 2023, the disclosures of which are incorporated herein by reference in their entireties for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 34,571 Byte Extensible Markup Language (XML) file named “FH00981US-Sequence-listing-2.xml,” created on Nov. 17, 2025.

FIELD OF THE INVENTION

The present application relates to the field of biotechnology, specifically to an RNA comprising a poly (A) tail. The poly (A) tail makes the replication of the DNA encoding the RNA in prokaryotic system more stable, and can be used to regulate the expression level of the RNA in an eukaryotic cell.

BACKGROUND OF THE INVENTION

The primary structure of a translatable mRNA drug molecule consists of a 5' cap structure, a 5' non-coding region (5' UTR), a coding region, a 3' non-coding region, and a polyadenosine tail (poly (A) tail). The known functions of the poly (A) tail include maintaining the in vivo stability of mRNA molecules and participating in the initiation of protein translation, the latter of which is achieved through the interaction between the poly (A) tail binding protein (PABP) and the translation initiation complex. In an eukaryotic cell, the poly (A) tail is synthesized by a post-transcriptional modification under the action of typical poly (A) polymerase.

The first step in preparing mRNA drugs in vitro is that the mRNA drugs are synthesized through in vitro transcription (IVT) by using a linearized plasmid containing the designed product sequence as a template, and the poly (A) tail is usually added downstream of the 3' UTR in a co-transcriptional manner. To achieve co-transcriptional addition of poly (A), the corresponding poly (dA:dT) sequence needs to be included in the template plasmid. However, the poly(dA:dT) repeat sequence in the plasmid is unstable during replication in *E. coli*, with deletion mutations often occur in such sequence, leading to the shortening of poly (dA:dT). This phenomenon is not conducive to the preparation process of in vitro transcription template plasmids through large scale fermentation, and the poly (A) truncation has a significant impact on the in vivo stability and biological activity of mRNA.

SUMMARY OF THE INVENTION

The present application provides a new poly (A) tail to enhance its conservation during preparation process in vitro.

Furthermore, a method for regulating the expression level of RNA in an eukaryotic cell based on the poly (A) tail is also provided.

Specifically, the first aspect of the present application provides an engineered DNA molecule capable of being replicated in a cell, comprising a polyadenosine tail (Poly A tail) coding sequence, wherein the poly (A) tail coding sequence comprises:

- a single element a and at least one element b, and at least one element c;
- a single element a and at least one element b, and at least one element d; or
- a single element a and at least one element b, and at least one element c and at least one element d,
  - in the poly (A) tail coding sequence, the element a consists of a plurality of consecutive adenine (A) nucleotides, and the length range of the element a is ≥20 nt;
  - the element b consists of a plurality of consecutive A nucleotides, and the length range of the element b is 3 nt≤b<20 nt;
  - the element c consists of a non-A nucleotide, and the nucleotide is selected from T, C and G nucleotides;
  - the element d consists of any two or more consecutive nucleotides, and the nucleotides are selected from A, T, C and G nucleotides, wherein the nucleotides at the 5' terminus and 3' terminus of the element d are not A nucleotides, and the element d does not comprise 3 or more consecutive A nucleotides; and the length range of the element d is 2 nt≤d≤20 nt;
  - wherein the element a and element b are not adjacent, and the element c and element d are not adjacent, and
  - the poly (A) tail coding sequence does not comprise any two elements b that are adjacent to each other, does not comprise any two elements c that are adjacent to each other, and does not comprise any two elements d that are adjacent to each other.

In some embodiments, the poly (A) tail coding sequence further comprises a single one element e, wherein the element e consists of one or two consecutive A, which is located at the 3' terminus of the poly (A) tail coding sequence and is adjacent to the element d or element c.

In some embodiments, the poly (A) tail coding sequence does not comprise other elements except for element a, element b, element c, and element d.

In some embodiments, the poly (A) tail coding sequence does not comprise other elements except for element a, element b, element c, element d and element e.

In some embodiments, the poly (A) tail coding sequence comprises at least 2 elements d. In some embodiments, the poly (A) tail coding sequence comprises at least 2 elements c. In some embodiments, the poly (A) tail coding sequence comprises at least one element d and one element c.

In some embodiments, the number of the element b is 2-10, for example, 3, 4, 5, 6, 7, 8, or 9.

In some embodiments, the number of the element c is 0-10, for example, 1, 2, 3, 4, 5, 6, 7, 8, or 9.

In some embodiments, the number of the element d is 0-5, for example, 1, 2, 3, or 4.

In some embodiments, when element c and element d are exist simultaneously, the total number of elements c and elements d is 2-15, for example, 3, 4, 5, 6, 7, 8, 9, 10, 11, 12, 13 or 14.

In some embodiments, the number of the element a is 1, the number of the element b is 3, the number of the element c is 2, and the number of the element d is 1.

In some embodiments, the number of the element a is 1, the number of the element b is 4, the number of the element c is 4, and the number of the element d is 1.

In some embodiments, the number of the element a is 1, the number of the element b is 5, the number of the element c is 4, and the number of the element d is 1.

In some embodiments, the number of the element a is 1, the number of the element b is 3, the number of the element c is 3, and the number of the element d is 1.

In some embodiments, the number of the element a is 1, the number of the element b is 3, the number of the element c is 2, and the number of the element d is 1.

In some embodiments, the length range of the element a is ≤80 nt. In some embodiments, the element a is 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, 51 nt, 52 nt, 53 nt, 54 nt, 55 nt, 56 nt, 57 nt, 58 nt, 59 nt, 60 nt, 61 nt, 62 nt, 63 nt, 64 nt, 65 nt, 66 nt, 67 nt, 68 nt, 69 nt, 70 nt, 71 nt, 72 nt, 73 nt, 74 nt, 75 nt, 76 nt, 77 nt, 78 nt, or 79 nt.

In some embodiments, the element b is 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, or 19 nt in length.

In some embodiments, the length range of the element d is 2 nt≤d≤20 nt, 3-18 nt, 5-16 nt, 4-10 nt, or 6-12 nt, for example, 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt or 20 nt, preferably 6 nt.

In some embodiments, the length of the poly (A) tail coding sequence is greater than 40 nt, for example, 41 nt, 42 nt, 43 nt, 44 nt, 45 nt, 46 nt, 47 nt, 48 nt, 49 nt, 50 nt, 51 nt, 52 nt, 53 nt, 54 nt, 55 nt, 56 nt, 57 nt, 58 nt, 59 nt, 60 nt, 61 nt, 62 nt, 63 nt, 64 nt, 65 nt, 66 nt, 67 nt, 68 nt, 69 nt, 70 nt, 71 nt, 72 nt, 73 nt, 74 nt, 75 nt, 76 nt, 77 nt, 78 nt, 79 nt, 80 nt, 81 nt, 82 nt, 83 nt, 84 nt, 85 nt, 86 nt, 87 nt, 88 nt, 89 nt, 90 nt, 91 nt, 92 nt, 93 nt, 94 nt, 95 nt, 96 nt, 97 nt, 98 nt, 99 nt, 100 nt, 101 nt, 102 nt, 103 nt, 104 nt, 105 nt, 106 nt, 107 nt, 108 nt, 109 nt, 110 nt, 111 nt, 112 nt, 113 nt, 114 nt, 115 nt, 116 nt, 117 nt, 118 nt, 119 nt, 120 nt, 121 nt, 122 nt, 123 nt, 124 nt, 125 nt, 126 nt, 127 nt, 128 nt, 129 nt, 130 nt, 131 nt, 132 nt, 133 nt, 134 nt, 135 nt, 136 nt, 137 nt, 138 nt, 139 nt, 140 nt, 141 nt, 142 nt, 143 nt, 144 nt, 145 nt, 146 nt, 147 nt, 148 nt, 149 nt, 150 nt, 151 nt, 152 nt, 153 nt, 154 nt, 155 nt, 156 nt, 157 nt, 158 nt, 159 nt, 160 nt, 161 nt, 162 nt, 163 nt, 164 nt, 165 nt, 166 nt, 167 nt, 168 nt, 169 nt, 170 nt, 171 nt, 172 nt, 173 nt, 174 nt, 175 nt, 176 nt, 177 nt, 178 nt, 179 nt, 180 nt, 181 nt, 182 nt, 183 nt, 184 nt, 185 nt, 186 nt, 187 nt, 188 nt, 189 nt, 190 nt, 191 nt, 192 nt, 193 nt, 194 nt, 195 nt, 196 nt, 197 nt, 198 nt, 199 nt, 200 nt, 201 nt, 202 nt, 203 nt, 204 nt, 205 nt, 206 nt, 207 nt, 208 nt, 209 nt, 210 nt, 211 nt, 212 nt, 213 nt, 214 nt, 215 nt, 216 nt, 217 nt, 218 nt, 219 nt, 220 nt, 221 nt, 222 nt, 223 nt, 224 nt, 225 nt, 226 nt, 227 nt, 228 nt, 229 nt, 230 nt, 231 nt, 232 nt, 233 nt, 234 nt, 235 nt, 236 nt, 237 nt, 238 nt, 239 nt, 240 nt, 241 nt, 242 nt, 243 nt, 244 nt, 245 nt, 246 nt, 247 nt, 248 nt, 249 nt, 250 nt, 251 nt, 252 nt, 253 nt, 254 nt, 255 nt, 256 nt, 257 nt, 258 nt, 259 nt, 260 nt, 261 nt, 262 nt, 263 nt, 264 nt, 265 nt, 266 nt, 267 nt, 268 nt, 269 nt, 270 nt, 271 nt, 272 nt, 273 nt, 274 nt, 275 nt, 276 nt, 277 nt, 278 nt, 279 nt, 280 nt, 281 nt, 282 nt, 283 nt, 284 nt, 285 nt, 286 nt, 287 nt, 288 nt, 289 nt, 290 nt, 291 nt, 292 nt, 293 nt, 294 nt, 295 nt, 296 nt, 297 nt, 298 nt, 299 nt, 300 nt, 301 nt, 302 nt, 303 nt, 304 nt, 305 nt, 306 nt, 307 nt, 308 nt, 309 nt, 310 nt, 311 nt, 312 nt, 313 nt, 314 nt, 315 nt, 316 nt, 317 nt, 318 nt, 319 nt, 320 nt, 321 nt, 322 nt, 323 nt, 324 nt, 325 nt, 326 nt, 327 nt, 328 nt, 329 nt, 330 nt, 331 nt, 332 nt, 333 nt, 334 nt, 335 nt, 336 nt, 337 nt, 338 nt, 339 nt, 340 nt, 341 nt, 342 nt, 343 nt, 344 nt, 345 nt, 346 nt, 347 nt, 348 nt, 349 nt, 350 nt, 351 nt, 352 nt, 353 nt, 354 nt, 355 nt, 356 nt, 357 nt, 358 nt, 359 nt, 360 nt, 361 nt, 362 nt, 363 nt, 364 nt, 365 nt, 366 nt, 367 nt, 368 nt, 369 nt, 370 nt, 371 nt, 372 nt, 373 nt, 374 nt, 375 nt, 376 nt, 377 nt, 378 nt, 379 nt, 380 nt, 381 nt, 382 nt, 383 nt, 384 nt, 385 nt, 386 nt, 387 nt, 388 nt, 389 nt, 390 nt, 391 nt, 392 nt, 393 nt, 394 nt, 395 nt, 396 nt, 397 nt, 398 nt, 399 nt, or 400 nt, etc.

In some embodiments, 50% or more of the polynucleotides of element a are located in the 5' portion or 3' portion of the poly (A) tail coding sequence. In some embodiments, 50% or more of the polynucleotides of element a are located in the 5' portion of the poly (A) tail coding sequence. In some embodiments, 50% or more of the polynucleotides of element a are located in the 3' portion of the poly (A) tail coding sequence. In some embodiments, the number of nucleotides of element a located at the 3' portion of the poly (A) tail coding sequence is equal to the number of nucleotides located at the 5' portion of the poly (A) tail coding sequence.

In some embodiments, the element c is G, C or T.

In some embodiments, the element d comprises a palindromic sequence. The element d is a palindromic sequence. In some embodiments, the element d comprises a sequence selected from the group consisting of GATATC (SEQ ID NO: 15), GTATAC (SEQ ID NO: 16), GAATCT (SEQ ID NO: 17), GCATATGACT (SEQ ID NO: 18), and GATATCGTATAC (SEQ ID NO: 19). In some embodiments, the element d is a sequence selected from the group consisting of GATATC (SEQ ID NO: 15), GTATAC (SEQ ID NO: 16), GAATCT (SEQ ID NO: 17), GCATATGACT (SEQ ID NO: 18), and GATATCGTATAC (SEQ ID NO: 19). In some embodiments, the element d comprises a polynucleotide sequence represented by SEQ ID NO: 15. In some embodiments, the polynucleotide sequence of element d is represented by SEQ ID NO: 15.

In some embodiments, the nucleotide at the 3' terminus of the poly (A) tail coding sequence is A. In some embodiments, the nucleotide at the 3' terminus of the poly (A) tail coding sequence is G. In some embodiments, the nucleotide at the 3' terminus of the poly (A) tail coding sequence is C. In some embodiments, the nucleotide at the 3' terminus of the poly (A) tail coding sequence is T.

In some embodiments, the 3' portion of the poly (A) tail coding sequence comprises one or more non-A nucleotides. In some embodiments, ½ portion of the poly (A) tail coding sequence near the 3' terminus comprises one or more non-A nucleotides. In some embodiments, ⅓ portion of the poly (A) tail coding sequence near the 3' terminus comprises one or more non-A nucleotides. In some embodiments, ¼ portion of the poly (A) tail coding sequence near the 3' terminus comprises one or more non-A nucleotides.

In some embodiments, the structure of the poly (A) tail coding sequence is:

element a-element c-element b-element c-element b-element c-element b-element c-element b;

element b-element c-element b-element c-element a-element d-element b-element c-element b-element c-element b;

element b-element c-element b-element c-element b-element d-element a-element c;

element a-element d-element b-element c-element b-element c-element b; or element b-element c-element b-element c-element b-element d-element a.

In some embodiments, the structure of the poly (A) tail coding sequence is:

element a-element c-element b-element c-element b-element c-element b-element c-element b; specifically, 60A-G-19A-G-19A-G-19A-G-3A.

In some embodiments, the structure of the poly (A) tail coding sequence is:

7A-C-18A-G-60A-GG-7A-C-18A-G-14A,
19A-G-19A-G-19A-element d-60A-G,
60A-element d-19A-G-19A-G-17A,
19A-G-19A-G-19A-element d-60A,
19A-G-19A-G-19A-element d-60A,
19A-C-19A-C-19A-element d-60A,
19A-T-19A-T-19A-element d-60A,
19A-G-19A-G-19A-element d-60A, or
19A-G-19A-G-19A-element d-60A; and
wherein the element d consists of 6 or 12 nucleotides.

In some embodiments, the poly (A) tail coding sequence is represented by any one of SEQ ID NOs: 1-10.

In some embodiments, the poly (A) tail coding sequence is represented by SEQ ID NO: 3 or SEQ ID NO: 4.

In some embodiments, the engineered DNA molecule is further connected to a gene of interest fragment on the 5' end side of its poly (A) tail coding sequence, wherein the gene of interest fragment and the poly (A) tail coding sequence co-encode RNA. In some embodiments, the engineered DNA molecule is further connected to a gene of interest fragment on the 5' end side of its poly (A) tail coding sequence, wherein the gene of interest fragment and the poly (A) tail coding sequence co-encode mRNA. In some embodiments, the gene of interest fragment comprises a protein coding sequence or a non-protein coding sequence, such as a functional RNA coding sequence. In some embodiments, the gene of interest fragment further comprises a 5'UTR coding sequence on the 5' end side of the protein coding sequence or the functional RNA coding sequence. In some embodiments, the gene of interest fragment further comprises a 3' UTR coding sequence on the 3' end side of the protein coding sequence or the functional RNA coding sequence. In some embodiments, the gene of interest fragment further comprises a 3' UTR coding sequence on the 3' end side of the protein coding sequence or the functional RNA coding sequence, and further comprises a 5' UTR coding sequence on the 5' end side of the protein coding sequence or the functional RNA coding sequence. In some embodiments, the engineered DNA molecule further comprises a replicon, for example, an origin of replication, such as an ORI. In some embodiments, the engineered DNA molecule further comprises a label gene in order to facilitate screening of cells comprising the engineered DNA molecule, and the label gene is selected from, for example, antibiotic resistance gene, fluorescent protein, and the like. In some embodiments, the DNA molecule further comprises a promoter, which initiates the transcription of RNA co-encoded by the gene of interest fragment and the poly (A) tail coding sequence. In some embodiments, the promoter is a prokaryotic promoter. In some embodiments, the promoter is an eukaryotic promoter. In some embodiments, the DNA molecule further comprises a replicon, for example, an origin of replication, a promoter, a 5' UTR coding sequence, a protein coding sequence, and a 3' UTR coding sequence. In some embodiments, the DNA molecule further comprises a replicon, for example, an origin of replication, a resistance gene, a 5' UTR coding sequence, a protein coding sequence, and a 3' UTR coding sequence. In some embodiments, the DNA molecule further comprises a replicon, for example, an origin of replication, a resistance gene, a promoter, a 5' UTR coding sequence, a protein coding sequence, and a 3' UTR coding sequence. In some embodiments, the protein coding sequence encodes an HPV viral antigen protein. In some embodiments, the HPV protein is derived from HPV type 16 and/or type 18. In some embodiments, the protein coding sequence encodes the E2, E6 or E7 protein of HPV. In some embodiments, the protein coding sequence encodes a fusion protein of the E6 and E7 proteins of HPV. In some embodiments, the protein coding sequence encodes a fusion protein of the E2, E6 and E7 proteins of HPV. In some embodiments, the polypeptide fragments of the fusion protein are derived from HPV type 16 and/or type 18. In some embodiments, the polypeptide fragments of the fusion protein are derived from E2, E6 and E7 proteins of HPV type 16 and/or type 18. In some embodiments, the protein coding sequence encodes a polypeptide represented by SEQ NO: 26 or a conservatively substituted variant thereof.

In some embodiments, the engineered DNA molecule comprises a polynucleotide sequence represented by any one of SEQ ID NOs: 22-25 or a synonymous mutant thereof, or a polynucleotide sequence sharing 85% or more sequence identity with the polynucleotide sequence represented by any one of SEQ ID NOs: 22-25 or a synonymous mutant thereof.

In some embodiments, the DNA molecule is a DNA plasmid. In some embodiments, the DNA molecule is a linear plasmid or a circular plasmid. In some embodiments, the DNA molecule is single-stranded or double-stranded. In some embodiments, the plasmid is a pUC-, pTZ-, pMB1-, or pCoIE1-based plasmid. In some embodiments, the plasmid is a pUC57 vector-based plasmid.

In some embodiments, the cell is a prokaryotic cell. In some embodiments, the cell is a recA-bacterium. In some embodiments, the cell is *Escherichia coli*. In some embodiments, the *E. coli* is selected from the group consisting of K-12 and derivative strains thereof, and B strain and derivative strains thereof. In some embodiments, the *E. coli* is selected from the group consisting of MG1655, DH5 or DH5a, DH10B, BL21, DB3.1™, HB101, JM109, JM110, MC1061, MG1655, Pir1, Stb12™, Stb13™, Top10, XL1 Blue®, XL10 Gold®, BLR, HMS174, Tuner™, Rostetta™2, Lemo21, T7Express, and Origami2™.

The second aspect of the present application discloses a cell comprising the DNA molecule of the first aspect. In some embodiments, the DNA molecule of the aforementioned first aspect can be replicated and/or transcribed in the cell. In some embodiments, the cell is a prokaryotic cell, and the DNA molecule of the aforementioned first aspect can be replicated in the prokaryotic cell. In some embodiments, the cell is a recA-bacterium. In some embodiments, the cell is *E. coli*. In some embodiments, the prokaryotic cell is a competent cell. In some embodiments, the prokaryotic cell is an engineered cell. In some embodiments, the prokaryotic cell is an engineered prokaryotic cell. In some embodiments, the cell is *E. coli*, and the *E. coli* is selected from the group consisting of K-12 and derivatives thereof, and B strain and derivatives thereof. In some embodiments, the *E. coli* is selected from the group consisting of MG1655, DH5 or DH5a, DH10B, BL21, DB3.1™, HB101, JM109, JM110, MC1061, MG1655, Pir1, Stb12™, Stb13™, Top10, XL1 Blue®, XL10 Gold®, BLR, HMS174, Tuner™, Rostetta™2, Lemo21, T7 Express, and Origami2™. In some embodiments, the cell is an eukaryotic cell, and the DNA molecule of the aforementioned first aspect can be transcribed in the eukaryotic cell. In some embodiments, the eukaryotic cell is a mammalian cell. In some embodiments, the eukaryotic cell is selected from the group consisting of a yeast or a mold.

In a third aspect of the present application, a poly (A) tail is provided. The poly (A) tail is:

(1) obtained by transcription of the engineered DNA molecule according to the first aspect;

(2) obtained by chemical synthesis, and has the same polynucleotide sequence as the poly (A) tail obtained by transcription of the engineered DNA molecule according to the first aspect; or (3) obtained by further modification of the poly (A) tail in the above item (1) or (2).

In some embodiments, the further modification comprises substituting one or more ribonucleotides in the poly (A) tail obtained by the above item (1) or (2) with one or more deoxyribonucleotides. In some embodiments, the one or more ribonucleotides are substituted with deoxyribonucleotides to which they correspond, for example, one or more ribonucleotides A of the poly (A) tail are substituted with deoxyribonucleotides A, one or more ribonucleotides U are substituted with deoxyribonucleotides T, one or more ribonucleotides C are substituted with deoxyribonucleotides C, one or more ribonucleotides G are substituted with deoxyribonucleotides G, or one or more ribonucleotides G are substituted with ribonucleotides I (inosine) or deoxyribonucleotides I. In some embodiments, the modification is a chemical modification. In some embodiments, the modification is base editing. In some embodiments, the modification is deamination treatment of one or more ribonucleotides in the poly (A) tail obtained by the above item (1) or (2).

In some embodiments, the poly (A) tail comprises a polynucleotide sequence selected from any one of SEQ ID NOs: 1-10. In some embodiments, the polynucleotide sequence of the poly (A) tail is represented by any one of SEQ ID NOs: 1-10.

The present application also provides use of the aforementioned poly (A) tail. In some embodiments, a use of the poly (A) tail for making an RNA molecule more stable is provided, wherein the poly (A) tail is located at the 3' terminus of the RNA, and the more stable means being more stable outside a cell, inside a cell, or in an animal body relative to an RNA molecule comprising an another poly (A) tail. In some embodiments, a use of the poly (A) tail for reducing the stability of an RNA molecule is provided, wherein the poly (A) tail is located at the 3' terminus of the RNA, and the reducing the stability refers to a reduced stability outside a cell, inside a cell, or in an animal body relative to an RNA molecule comprising an another poly (A) tail. In some embodiments, a use of the poly (A) tail for increasing the expression level of an RNA molecule in the same period is provided, wherein the increasing the expression level refers to an increased expression level outside a cell, inside a cell, or in an animal body relative to an RNA molecule comprising an another poly (A) tail. In some embodiments, a use of the poly (A) tail for reducing the expression level of an RNA molecule within the same period is provided, wherein the educing the expression level refers to a reduced expression level outside a cell, inside a cell, or in an animal body relative to an RNA molecule comprising an another poly (A) tail. In some embodiments, a use of the poly (A) tail for prolonging the expression time of an RNA molecule is provided, wherein the prolonging the expression time refers to a prolonged expression time outside a cell, inside a cell, or in an animal body relative to an RNA molecule comprising an another poly (A) tail. In some embodiments, a use of the poly (A) tail for shortening the expression time of an RNA molecule is provided, wherein the shortening the expression time refers to a shortened expression time outside a cell, inside a cell, or in an animal body relative to an RNA molecule comprising an another poly (A) tail. In some embodiments, a use of the poly (A) tail for extending the half-life of an RNA molecule is provided, wherein the extending the half-life refers to an extended half-life outside a cell, inside a cell, or in an animal body relative to an RNA molecule comprising an another poly (A) tail. In some embodiments, a use of the poly (A) tail for shortening the half-life of an RNA molecule is provided, wherein the shortening the half-life refers to a shortened half-life outside a cell, inside a cell, or in an animal body relative to an RNA molecule comprising an another poly (A) tail.

In some embodiments, the RNA molecule is an mRNA molecule. In some embodiments, the poly (A) tail and the other poly (A) tail are two different poly (A) tails that belong to the poly (A) tail according to the third aspect of the present application. In some embodiments, the poly (A) tail is the poly (A) tail according to the third aspect of the present application, and the other poly (A) tail is a poly (A) tail other than the poly (A) tail according to the third aspect of the present application. In some embodiments, the inside a cell means inside a host cell, and the host cell is an eukaryotic cell. In some embodiments, the host cell is a mammalian cell. In some embodiments, the host cell is a human cell.

The present application also provides a DNA fragment or a hybrid molecule fragment of DNA and RNA for encoding the poly (A) tail according to the third aspect of the present application, and a use of the DNA fragment or the hybrid molecule fragment of DNA and RNA for making the replication of the DNA molecule or the hybrid molecule of DNA and RNA for encoding an RNA more conservative in a host cell, and in said use, wherein the DNA fragment or the hybrid molecule fragment of DNA and RNA for encoding the poly (A) tail according to the third aspect of the present application is located on the 3' end side of the RNA coding sequence in the DNA molecule or the hybrid molecule of DNA and RNA. In some embodiments, the host cell is a prokaryotic cell. In some embodiments, the host cell is a recA-bacterium. In some embodiments, the host cell is *E. coli*. In some embodiments, the *E. coli* is selected from the group consisting of K-12 and derivative strains thereof, and B strain and derivative strains thereof. In some embodiments, the *E. coli* is selected from the group consisting of MG1655, DH5 or DH5a, DH10B, BL21, DB3.1™, HB101, JM109, JM110, MC1061, MG1655, Pir1, Stb12™, Stb13™, Top10, XL1Blue®, XL10Gold®, BLR, HMS174, Tuner™, Rostetta™2, Lemo21, T7Express, and Origami2™.

The fourth aspect of the present application also provides an RNA molecule, wherein it comprises the poly (A) tail according to the third aspect. In some embodiments, the RNA molecule is an mRNA molecule. In some embodiments, the RNA molecule is:

(1) obtained by transcription of the engineered DNA molecule according to the first aspect;

(2) obtained by chemical synthesis, and has the same polynucleotide sequence as the RNA molecule of the above item (1); or (3) obtained by further modification of the RNA molecule in above item (1) or (2).

In some embodiments, the further modification comprises substituting one or more ribonucleotides in the RNA molecule obtained by the above (1) or (2) with one or more deoxyribonucleotides. In some embodiments, the one or more ribonucleotides are substituted with deoxyribonucleotides to which they correspond, for example, one or more ribonucleotides A of the RNA molecule are substituted with deoxyribonucleotides A, one or more ribonucleotides U are substituted with deoxyribonucleotides T, one or more ribonucleotides C are substituted with deoxyribonucleotides C, one or more ribonucleotides G are substituted with deoxyribonucleotides G, or one or more ribonucleotides G are substituted with ribonucleotides I (inosine) or deoxyribonucleotides I. In some embodiments, the modification is a chemical modification. In some embodiments, the modification is base editing. In some embodiments, the modification is deamination treatment of one or more ribonucleotides in the RNA molecule obtained by the above (1) or (2). In some embodiments, the further modification is a post-transcriptional modification. In some embodiments, the further modification comprises capping treatment. In some embodiments, the further modification comprises splicing. In some embodiments, the further modification comprises splicing and capping treatment.

In some embodiments, the RNA molecule comprises coding RNA or non-coding RNA (ncRNA). In some embodiments, the RNA molecule is a pre-mRNA. In some embodiments, the RNA is a mature mRNA. In some embodiments, the RNA molecule is a long non-coding RNA (lncRNA). In some embodiments, the RNA molecule further comprises a 5'-cap structure. In some embodiments, the polynucleotide sequence of the RNA molecule is represented by any one of SEQ ID NOs: 22-25. In some embodiments, the RNA molecule comprises a polynucleotide sequence represented by any one of SEQ ID NOs: 22-25.

In addition, the present application also provides a hybrid molecule of DNA and RNA, which carries the same genetic information as the engineered DNA molecule according to the first aspect, the same genetic information as the poly (A) tail according to the third aspect, or the same genetic information as the RNA molecule according to the fourth aspect.

In addition, the present application also provides a nucleic acid molecule library. In some embodiments, the nucleic acid molecule library comprises the engineered DNA molecule according to the first aspect, the poly (A) tail according to the third aspect, the DNA fragment or the hybrid molecule fragment of DNA and RNA for encoding the poly (A) tail according to the third aspect of the present application, or the RNA molecule according to the fourth aspect.

In addition, the present application also provides a method for regulating protein expression, which comprises introducing a plurality of nucleic acid molecules in the aforementioned nucleic acid molecule library into cells of interest at different times and/or in different quantity ratios. In some embodiments, the nucleic acid molecule is the engineered DNA molecule according to the aforementioned first aspect. In some embodiments, the nucleic acid molecule is the RNA molecule according to the aforementioned fourth aspect.

It should be understood that aspects and embodiments according to the present application described herein include the aspects and embodiments that "comprise/comprising", "consist/consisting of", and "essentially consist/consisting of" the same. The preferred embodiments of the present application are described in detail above; however, the present application is not limited thereto. Within the technical concept of the present application, a variety of simple modifications can be made to the technical solutions of the present application, including combinations of various technical features in any other suitable manner. These simple modifications and combinations should also be regarded as the contents disclosed in the present application, and belong to the protection scope of the present application.

BACKGROUND OF THE INVENTION

Figure 1:
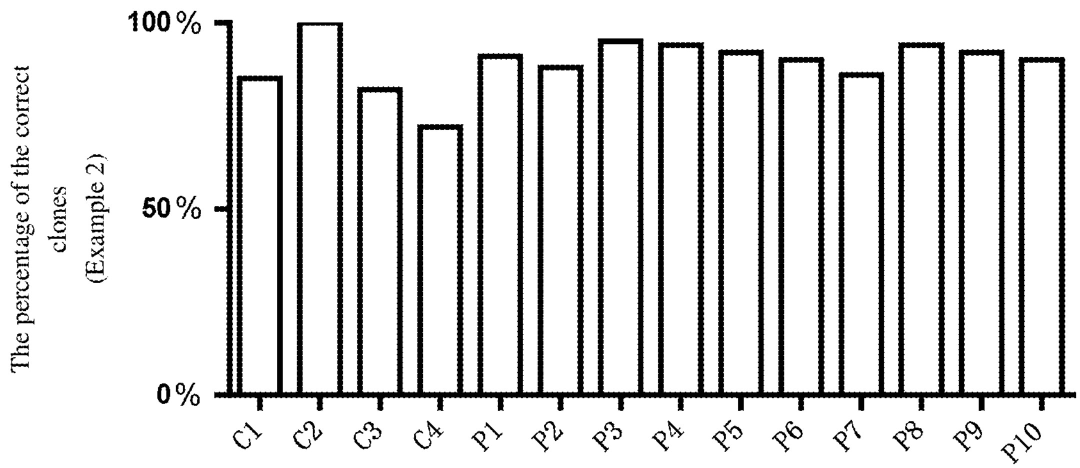
FIG. 1 shows the replication stability of 10 poly (A) s in the present application in *E. coli* DH5a in Example 2.

The present application firstly provides a method for stably amplifying a poly (A) tail transcription template DNA in vitro, so as to reduce the mutation frequency of the poly (A) tail transcription template sequence when the DNA is replicated in large quantities in a cell. Thus, a large amount of RNA comprising a poly (A) tail with a defined sequence is obtained based on the DNA. On this basis, RNA with a poly (A) tail that is engineered to have a specific function, such as a mRNA, can be produced on a large scale through in vitro fermentation.

In addition, the present application also provides a DNA comprising a poly (A) tail transcription template that can be stably amplified in vitro, and an RNA transcribed from the DNA. Furthermore, under the premise of satisfying in vitro stable amplification, the present application further provides a group of poly (A) tails having different regulatory effects on RNA stability and/or expression efficiency, an RNA comprising the poly (A) tail, a DNA comprising the poly (A) tail coding sequence, and a library consisting of the poly (A) tail, the RNA or the DNA.

Furthermore, the present application also provides uses of the aforementioned poly (A) tail, RNA, DNA, and library.

Terms

As used herein, "element a", "element b", "element c", "element d", and "element e" are types of elements comprised in poly (A). The element a consists of a plurality of consecutive adenine (A) nucleotides, and the length range of element a is ≥20 nt; the element b consists of a plurality of consecutive A nucleotides, and the length range of element b is 3 nt≤b<20 nt; the element c consists of a non-A nucleotide, and the nucleotide is selected from T, C and G nucleotides; the element d consists of any two or more consecutive nucleotides, and the nucleotides are selected from A, T, C and G nucleotides, wherein the nucleotides at the 5' terminus and 3' terminus of element d are not A nucleotides, and the element d does not comprise 3 or more consecutive A nucleotides, and the length range of element d is 2 nt≤d≤20 nt. The element e consists of one or two consecutive A, and the element e is located at the 3'end of the poly (A) tail coding sequence and is adjacent to the element d or the element c when it exists. When the poly (A) sicomprises two or more “element b”, “element c”, and “element d”, the sequences of each two elements b may be the same or different, the sequences of each two elements c may be the same or different, and the sequences of each two elements d may be the same or different, as long as they each meet the above definitions of elements a, b, c and d. In the present application, the “element a”, “element b”, “element c”, “element d”, “element e”, etc. in the poly (A) tail may be indicated by the term “element”.

As used herein, when describing the positional relationship of two or more elements as “non-adjacent”, it means that the two or more elements are not adjacent to each other. In other words, the two or more elements at least comprise one or more other nucleotides or bases other than the nucleotides of the two elements between each two elements.

As used herein, “encoding\coding” means i) a DNA sequence comprising genetic information that can be transcribed into an RNA molecule, and/or ii) an RNA molecule comprising genetic information that can be translated into an amino acid sequence. As used herein, therefore, the “coding sequence” refers to a ribonucleotide (RNA) sequence or a fragment thereof in a mRNA precursor or a mature mRNA that can be translated into a protein, and also refers to a complementary sequence or a fragment thereof of a deoxyribonucleotide (DNA) sequence that serves as a template for transcribing the mRNA precursor or mature mRNA. In addition, the “coding sequence” of the present application may further comprise polynucleotide sequences encoding proteins, functional nucleic acids, or fragments thereof, such as miRNA, shRNA, dsRNA, guide RNA, poly (A) tail, 5' UTR, 3' UTR, etc. Among them, a DNA molecule comprising genetic information that can be transcribed into an RNA molecule is called the “coding nucleic acid” of the RNA molecule; and an RNA molecule comprising genetic information that can be translated into an amino acid sequence is called the “coding nucleic acid” of the amino acid sequence.

In the present application, the nucleotides in all polynucleotide sequences are numbered from the 5' end to the 3' end, that is, the nucleotide at the 5' terminus is the first nucleotide, and the nucleotide at the 3' terminus is the last nucleotide. Unless otherwise specified, “5' end” and “5' terminus” can be used interchangeably; “3' end” and “3' terminus” can be used interchangeably. “5' end” and “3' end” focus on describing the relative position relationship between nucleotides, between nucleotide sequence segments, or between nucleotides and nucleotide sequence segments in the same nucleic acid sequence; “5' terminus” and “3' terminus” are used to describe the positions of the first and last nucleotides of a nucleic acid sequence or a segment of a nucleic acid sequence, respectively. “5' end side” is used to describe the relative position relationship between two non-overlapping sequences in the same polynucleotide sequence; when describing a sequence being located on the 5' end side of another sequence, it means that the sequence is more closer to the “5' end” of the polynucleotide sequence compared to another sequence. Similarly, when describing that a sequence is located on the 3' end side of another sequence, it means that the sequence is closer to the “3' end” of the polynucleotide sequence compared to another sequence, moreover, the sequence and another sequence do not comprise any overlapping parts each other. Specifically, for example, “the DNA coding sequence of the poly (A) tail is located at the 3' end of the RNA coding sequence” means that the DNA coding sequence of the poly (A) tail, as the component of the RNA coding sequence, comprises the nucleotides at the 3' terminus of the RNA coding sequence. In addition, as used herein, the “5' portion” refers to the one that near the half of the 5' terminus of the polynucleotide sequence, bounded by the “center position” of the polynucleotide sequence. The “3' portion” refers to the one that near the half of the 3' terminus of the polynucleotide sequence, bounded by the center position of the polynucleotide sequence. The number of nucleotides from the “central position” as described in this application to the 5' end is equal to the number of nucleotides from the “central position” as described in this application to the 3' end.

As used herein, when referring to the replication of a nucleic acid molecule, the term “conservative” means a low probability of mutation during the replication process. In this context, the “conservative” is a relative concept. For example, when describing that “the DNA coding sequence of the poly (A) tail is used to make the replication of the DNA molecule coding RNA more conservative in the host cell”, it refers to the probability that the parent DNA molecule encoding RNA replicates into an offspring DNA molecule. If the RNA molecule comprises the Poly (A) tail, the offspring DNA molecule has a higher probability of 100% sequence identity with the parent DNA molecule compared to the coding DNA of an RNA molecule that does not comprise the Poly (A) tail (such as an RNA molecule comprising some other Poly (A) tail); the average sequence identity between multiple offspring DNA molecules obtained by replication of the parent DNA molecule and the parent DNA molecule is higher.

In the present application, when describing “regulating” the expression of an RNA molecule, the “regulating” means increasing or decreasing the total amount of the protein or functional RNA expressed by the RNA molecule within the same time period; or enabling the RNA to express the protein or functional RNA within a longer or shorter time period, and the increased or decreased, or longer or shorter time period is compared to another RNA molecule expressing the same protein or functional RNA. When describing “regulating” protein expression, it means regulating the expression of RNA molecules comprising the protein coding sequence. The regulatory effect described herein can be achieved by connecting the poly (A) tail of the present application to the 3' terminus of an RNA molecule that does not comprise a poly (A) tail, or by substituting the original poly (A) tail of the RNA with the poly (A) tail of the present application.

As used herein, the percentage of “identity”, for example 85%, 90%, 91%, 92%, 93%, 94%, 95%, 96%, 97%, 98%, 98.5%, 99%, or 99.5% identity, refers to the degree of similarity between amino acid sequences or between nucleotide sequences, as determined by sequence alignment, which is 85%, 90%, 91%, 92%, 93%, 94%, 95%, 96%, 97%, 98%, 98.5%, 99%, or 99.5%. For example, after two sequences have identical residues at as many positions as possible by introducing gaps, the ratio of the number of positions occupied by the identical bases or amino acid residues to the total number of positions is determined. The percentage of “identity” can be determined by using software programs known in the art. Preferably the alignment is performed by using default parameters. A preferred alignment program is BLAST. Preferred programs are BLASTN and BLASTP. Details of these programs are available at the following: ncbi.nlm.nih.gov/cgi-bin/BLAST.

As used herein, nucleic acid "complementarity" refers to the ability of one nucleic acid to form hydrogen bonds with another nucleic acid through traditional Watson-Crick base-pairing. Percent complementarity refers to the percentage of residues in a nucleic acid molecule that can form hydrogen bonds (i.e., Watson-Crick base-pairing) with another nucleic acid molecule (e.g., about 5, 6, 7, 8, 9, 10 out of 10 correspond to about 50%, 60%, 70%, 80%, 90%, and 100% complementarity, respectively). "Completely complementary" means that all consecutive residues of a nucleic acid sequence will form hydrogen bond with the same number of consecutive residues in a second nucleic acid sequence. As used herein, "substantially complementary" refers to a degree of complementarity of any one of at least about 70%, 75%, 80%, 85%, 90%, 95%, 96%, 97%, 98%, 99%, or 100% over a region of about 40, 50, 60, 70, 80, 100, 150, 200, 250 or more nucleotides, or to two nucleic acids that hybridize under stringent conditions. For a single base or a single nucleotide, according to the Watson-Crick base-pairing principle, when A is paired with T or U, and C is paired with G or I, it is called complementary or matching, and vice versa; any other base-pairing is called non-complementary. In the present application, the "complementary polynucleotide sequence" of a certain polynucleotide sequence refers to a polynucleotide sequence that is completely complementary to the certain polynucleotide sequence.

As used herein, a "conservative substitution variant" of a protein, polypeptide or amino acid sequence refers to one in which one or more amino acid residues are subjected to amino acid substitution without altering the overall conformation and function of the protein or enzyme, including but not limited to substituting the amino acids in the amino acid sequence of the parent protein in the manner described by the aforementioned "conservative substitution". Therefore, the similarity between two proteins or amino acid sequences with similar functions may be different. For example, 70-99% similarity (identity) based on the MEGALIGN algorithm. The "conservative substitution variants" also comprise polypeptides or enzymes with 60% or more amino acid identity as determined by BLAST or FASTA algorithms, preferably 75% or more, more preferably 85% or more, and most preferably even 90% or more, and have the same or substantially similar properties or functions as the native or parent protein or enzyme.

In the context of this application, the terms "DNA" and "RNA" refer to single-stranded or double-stranded DNA or RNA molecules. Unless otherwise indicated, the terms "DNA" and "DNA molecule" refer to double-stranded DNA molecules composed of A, C, G and/or T nucleotides, and the terms "RNA" and "RNA molecule" refer to single-stranded RNA molecules composed of A, C, G and/or U nucleotides. Herein, the A, C, G, T and U nucleotides refer to nucleotides comprising adenine, guanine, cytosine, thymine and uracil as respective nitrogenous bases.

RNA molecules comprise coding RNA or non-coding RNA (ncRNA), such as pre-mRNA, mature mRNA, or long non-coding RNA (lncRNA).

As used herein, the "hybrid molecule of DNA and RNA" is a molecule comprising a polynucleotide sequence consisting of deoxyribonucleotides and ribonucleotides. The hybrid molecule of DNA and RNA can be obtained by the following method:

substituting one or more deoxyribonucleotides in the DNA with ribonucleotides;

substituting one or more ribonucleotides in the RNA with deoxyribonucleotides; or de novo synthesizing by using deoxyribonucleotides and ribonucleotides as raw materials through biological or chemical synthesis. It should be noted that the method of obtaining a hybrid molecule of DNA and RNA is not limited to the above method, and a hybrid molecule of DNA and RNA obtained by any method belong to the category of "a hybrid molecule of DNA and RNA" defined in this application.

As used herein, when describing two nucleic acid molecules as having "the same genetic information", it means that the two nucleic acid molecules are complementary, or comprise exactly the same base sequence, or one nucleic acid molecule having exactly the same base sequence as another nucleic acid molecule can be obtained by converting one or more thymines in the base sequence of one nucleic acid molecule into uracil. Therefore, any two of the DNA, RNA, and a hybrid molecule of DNA and RNA can have the same genetic information. Herein, the term "base sequence" refers to the order of arrangement of bases in a polynucleotide molecule. Unless otherwise specified, those skilled in the art should be understood that the thymine may be indicated by "T" when the base sequence or polynucleotide sequence described in the present application are used to describe a DNA sequence, while the "T" will be substituted by "U" (uracil) when the base sequence or polynucleotide sequence are used to describe RNA (such as mRNA). Therefore, whenever a DNA is disclosed by a specific sequence number (SEQ ID NO) herein, an RNA (e.g. mRNA or poly (A) tail) sequence complementary or corresponding to the DNA is also disclosed, wherein each "T" in the DNA sequence is substituted by a "U".

Poly (A) Tail and Uses Thereof

As used herein, the term "Poly A tail" or "Poly (A) sequence" refers to an uninterrupted or non-interrupted sequence of adenylate residues typically located at the 3'-terminus of an RNA molecule. In RNA, in the presence of a 3'-UTR, the Poly-A sequence is linked to the 3' end of the 3'-UTR. An uninterrupted Poly-A tail is characterized by consecutive adenylate residues. The Poly-A tail can be of any length. In some embodiments, the Poly-A tail comprises, or consists of, at least 20, at least 30, at least 40, at least 80 or at least 100, and at most 500, at most 400, at most 300, at most 200 or at most 150 adenylate nucleotides (A), in particular about 120 A. Typically, the vast majority of nucleotides in the Poly-A tail are adenosines, wherein the vast majority refers to at least 75%, at least 80%, at least 85%, at least 90% of the nucleotides, etc., but the remaining nucleotides are allowed to be nucleotides other than A (non-A nucleotides), such as U (uridylic acid), G (guanylic acid) or C (cytidylic acid).

In some embodiments, the in vitro preparation process of the RNA is a prokaryotic fermentation process, that is, the coding nucleic acid of the RNA molecule comprising the poly (A) tail is introduced into prokaryotic cells, and the prokaryotic cells are amplified to achieve the purpose of amplifying the coding nucleic acid, and then the amplified coding nucleic acid is transcribed into the RNA. In some embodiments, the in vitro preparation process of the RNA is to connect an RNA fragment comprising a protein coding sequence to a poly (A) tail by homologous recombination, enzyme digestion and ligation, or other non-homologous recombination methods, and the poly (A) tail is prepared by a prokaryotic fermentation process. During the prokaryotic fermentation process, the coding nucleic acid comprising the poly (A) tail is introduced into prokaryotic cells, and the prokaryotic cells are amplified to achieve the purpose of amplifying the coding nucleic acid; subsequently, the amplified coding nucleic acid is transcribed into an RNA comprising the poly (A) tail. In some embodiments, the aforementioned coding nucleic acid is linear. In some embodiments, the aforementioned coding nucleic acid is circular. In some embodiments, the aforementioned coding nucleic acid is a plasmid. In some embodiments, the aforementioned coding nucleic acid is single-stranded or double-stranded. In some embodiments, the aforementioned coding nucleic acid is chemically modified before being introduced into a prokaryotic cell. In some embodiments, the aforementioned coding nucleic acid is chemically synthesized before being introduced into a prokaryotic cell. In some embodiments, the coding nucleic acid is inserted into the nucleoid/karyoid genomic DNA of the prokaryotic cell. In some embodiments, the coding nucleic acid is free in the cytoplasm or outside the nucleoid/karyoid of the prokaryotic cell. In some embodiments, the prokaryotic cell is *E. coli.*

Based on this, the present application provides a series of poly (A) tails, which are highly conserved during the in vitro preparation of RNA. The poly (A) tail comprises one or more non-A nucleotides at one or more positions.

In some embodiments, the poly (A) tail coding sequence comprises:

- a single element a and at least one element b, and at least one element c;
- a single element a and at least one element b, and at least one element d; or
- a single element a and at least one element b, and at least one element c and at least one element d,
- wherein the element a and element b are not adjacent, the element c and element d are not adjacent, and
- the poly (A) tail coding sequence does not comprise any two elements b adjacent to each other, does not comprise any two elements c adjacent to each other, and does not comprise any two elements d adjacent to each other.

In some embodiments, the poly (A) tail coding sequence further comprises a single element e, wherein the element e consists of one or two consecutive A, which is located at the 3' terminus of the poly (A) tail coding sequence, and is adjacent to element d or element c.

The poly (A) tail herein can be a segment of RNA, or a hybrid molecule of DNA and RNA.

The present application also provides a poly (A) tail that can regulate protein expression level. In addition, the present application also provides a poly (A) tail that can regulate protein expression level while maintaining highly conservative during the in vitro preparation process. In some embodiments, the poly (A) tail that can regulate protein expression level; or the poly (A) tail that can regulate protein expression level while maintaining highly conservative during the in vitro preparation process is selected from the group consisting of:

- element a-element c-element b-element c-element b-element c-element b-element c-element b;
- element b-element c-element b-element c-element a-element d-element b-element c-element b-element c-element b;
- element b-element c-element b-element c-element b-element d-element a-element c;
- element a-element d-element b-element c-element b-element c-element b; and
- element b-element c-element b-element c-element b-element d-element a.

In some embodiments, the poly (A) tail that can regulate protein expression level; or the poly (A) tail that can regulate protein expression level while maintaining highly conservative during the in vitro preparation process is selected from the group consisting of:

- 60A-G-19A-G-19A-G-19A-G-3A;
- 7A-C-18A-G-60A-element d-7A-C-18A-G-14A;
- 60A-element d-19A-G-19A-G-17A;
- 19A-G-19A-G-19A-element d-60A;
- 19A-G-19A-G-19A-element d-60A-G;
- 19A-G-19A-G-19A-element d-60A;
- 19A-C-19A-C-19A-element d-60A; and
- 19A-T-19A-T-19A-element d-60A.

In some embodiments, the poly (A) tail that can regulate protein expression level; or the poly (A) tail that can regulate protein expression level while maintaining highly conservative during the in vitro preparation process is: 60A-element d-19A-G-19A-G-17A or 19A-G-19A-G-19A-element d-60A.

Particularly, the two elements connected by "-" are directly connected, and there is no nucleotide between the two elements.

In the above-mentioned structure of the poly (A) tail, "yA" represents the number of consecutive A in element a or element b, wherein y is a natural number, for example, 19A means that it comprises 19 consecutive A; 60A means that it comprises 60 consecutive A.

In some embodiments, the poly (A) tail that can regulate protein expression level; or the poly (A) tail that can regulate protein expression level while maintaining highly conservative during the in vitro preparation process is selected from any one of the polynucleotide sequences represented by SEQ ID NOs: 1-10.

In addition, the present application also provides use of the above-mentioned poly (A) tail for regulating protein expression, wherein in said use, the poly (A) tail is located at the 3' end of the mRNA, such as the 3' end of the 3' UTR. In some embodiments, the regulating protein expression uses the method for regulating protein expression described below.

Engineered DNA Molecules and Libraries

The present application also provides an engineered DNA molecule that can replicate in a cell, which comprises the coding sequence of the aforementioned Poly A tail or a complementary sequence thereof. Those skilled in the art should be understood that, in addition to the coding sequence of the Poly A tail, the engineered DNA molecule should also comprise structural elements necessary for the DNA molecule to replicate or to replicate efficiently in a cell. The structural elements necessary for the DNA molecule to replicate or to replicate efficiently in a cell are known in the art and comprise, for example, an origin of replication (ORI). In some embodiments, the engineered DNA molecule further comprises a label gene or a fragment thereof, and/or a reporter gene or a fragment thereof, and a unique restriction endonuclease site allowing insertion of DNA elements, preferably a restriction endonuclease site that functions as a multiple cloning site (MCS). The label gene facilitates the identification of a cell containing a plasmid comprising the label gene, which may be selected from, for example, an antibiotic resistance gene. Each restriction endonuclease site in the MCS can be specifically recognized by a different restriction endonuclease.

In some embodiments, the DNA molecule is a DNA plasmid. As used herein, the term "DNA plasmid" refers to a plasmid consisting of a double-stranded DNA molecule. In some embodiments, the "plasmid" is a circular DNA molecule. In some embodiments, the "plasmid" may also encompass a linear DNA molecule. Specifically, the term "plasmid" also encompasses molecules obtained by linearizing a circular plasmid, for example by cleaving a circular plasmid with a restriction endonuclease, thereby converting the circular plasmid molecule into a linear molecule, as well as a linear molecule replicable in a prokaryote. A plasmid can be replicates, i.e., can be amplified in a cell independently of the genomic genetic information stored in a nucleoid or karyoid of a prokaryotic cell, and can be used for cloning, i.e., for amplifying genetic information in a bacterial cell. Preferably, the DNA plasmid according to the present application is a medium copy or high copy plasmid, more preferably a high copy plasmid. Examples of such high copy plasmids are vectors based on pUC, pTZ plasmids or any other plasmid comprising an ORI supporting high copy of the plasmid (e.g., pMB1, pCoIE1 etc.).

In some embodiments, the DNA molecule is a DNA molecule or a fragment thereof constituting a nucleoid or karyoid of a prokaryotic organism, that is, the coding sequence comprising the aforementioned poly (A) tail or a complementary sequence thereof can be replicated along with the prokaryotic genome.

In some embodiments, the DNA molecule is further connected to a gene of interest fragment on the 5' end side of the poly (A) tail coding sequence, and the gene of interest fragment and the poly (A) tail coding sequence co-encode RNA. In some embodiments, the gene of interest fragment and the poly (A) tail coding sequence co-encode mRNA. The gene of interest fragment comprises a coding sequence of a protein, a polypeptide or a fragment thereof. In some embodiments, the gene of interest fragment also comprises a coding sequence for an element that can be used to initiate or regulate the expression of the protein, polypeptide or a fragment thereof after transcription, and the elements include, but are not limited to, 5' UTR, 3' UTR, etc. In some embodiments, the gene of interest fragment comprises a coding sequence of at least one untranslated region (UTR). In some embodiments, the gene of interest fragment comprises at least the coding sequence of the 5' UTR and the coding sequence of the protein, polypeptide or a fragment thereof. In some embodiments, the gene of interest fragment comprises from 5' to 3' sequentially at least: the coding sequence of 5' UTR, the coding sequence of protein, polypeptide or a fragment thereof, and the coding sequence of 3' UTR. The coding sequence of the protein, polypeptide or a fragment thereof can be ultimately translated into one or more proteins, or one or more polypeptides, for example, short peptides, oligopeptides, polypeptides, fusion proteins, proteins and fragments thereof, such as parts of known proteins, such as functional parts. The functional portion can be, for example, a biologically active portion of a protein, or an antigenic portion that can effectively generate antibodies, such as an antigenic epitope. The two ends of the coding sequence of the protein, polypeptide or a fragment thereof respectively comprise a start codon (5' end) and a stop codon (3' end), which are respectively the first three nucleotides and the last three nucleotides of the mRNA molecule that can be translated. The 5' UTR usually comprises at least one ribosome binding site (RBS), such as the Shine-Dalgarno sequence in a prokaryote, or at least one translation start site, such as the Kozak sequence in a eukaryote. RBS promotes efficient and accurate translation of mRNA molecules by recruiting ribosomes upon the translation initiation. The activity of which can be optimized by varying the length and sequence of a given RBS or translation-initiating site, as well as the distance from the given RBS or translation-initiating site to the start codon. Alternatively or optionally, the 5' UTR comprises an internal ribosome entry site or IRES. The 3' UTR may comprise one or more regulatory sequences, for example binding sites for amino acid sequences that enhance the stability of the mRNA molecule, binding sites for regulatory RNA molecules (such as miRNA molecules), and/or signal sequences involved in the intracellular transport of mRNA molecules.

Based on the foregoing embodiments, in some embodiments, the gene of interest fragment further comprises one or more additional regulatory sequences, such as binding sites for amino acid sequences that enhance the stability of mRNA molecules, binding sites for amino acid sequences that enhance the translation of mRNA molecules, regulatory elements (such as riboswitches), binding sites for regulatory RNA molecules (such as miRNA molecules), and/or nucleotide sequences that positively affect translation initiation. Furthermore, within the 5' UTR, preferably there is no functional upstream open reading frame, out-of-frame upstream translation start site, out-of-frame upstream start codon, and/or nucleotide sequences that produce secondary structures that reduce or prevent translation. The presence of such nucleotide sequences in the 5' UTR may negatively affect translation.

The coding sequence of the protein, polypeptide or a fragment thereof comprises codons that can be translated into an amino acid sequence. All the codons comprised in the coding sequence may be naturally occurring codons coding amino acids or may be partially or entirely composed of artificially synthesized codons. In some embodiments, some or all of the codons are codon optimized. In some embodiments, some or all of the codons encode unnatural amino acids.

In some embodiments, the DNA molecule further comprises structural elements necessary for initiating or regulating transcription of the RNA on the 5' end side of the gene of interest fragment, and the structural elements are known in the art. In some embodiments, the structural element comprises at least a promoter. Promoters and their sequences are known in the art, including weak promoters, medium strength promoters, strong promoters, mini-promoters or core promoters, etc. In some specific embodiments, the promoter is a strong promoter. In some embodiments, the promoter can initiate transcription of the gene of interest fragment and/or poly (A) tail in a prokaryotic cell. In some embodiments, the promoter can initiate transcription of the gene of interest fragment and/or poly (A) tail in a eukaryotic cell. The "promoter" comprises at least one transcription recognition site followed by a transcription factor binding site. The recognition and binding sites may interact with an amino acid sequence that mediates or regulates transcription. Compared with the recognition site, the binding site is more closer to the aforementioned gene of interest fragment. The binding site may be, for example, a Pribnow box in a prokaryote or a TATA box in a eukaryote. For example, in some embodiments, when the Pribnow box is used, the transcription recognition site can be located about 35 bp upstream of the transcription start site, while the transcription factor binding site can be located about 10 bp upstream of the transcription start site. In some embodiments, the promoter comprises at least one additional regulatory element, for example an AT-rich upstream element located approximately 40 and/or 60 nucleotides before the transcription start site, and/or an additional regulatory element for enhancing promoter activity located between the recognition site and the binding site. In some embodiments, the promoter is a strong promoter, i.e., the promoter comprises a sequence for promoting the transcription of the aforementioned RNA coding sequence. Strong promoters are known to those skilled in the art, such as the OXB18, OXB19 and OXB20 promoters derived from the RecA promoter of *E. coli* or can be identified or synthesized by routine laboratory procedures. In some embodiments, the promoter is a T7 promoter. In some embodiments, the promoter further comprises additional regulatory elements, such as an enhancer comprised in the DNA plasmid that can promote the transcription of the aforementioned RNA coding sequence.

The present application also provides a library comprising the aforementioned engineered DNA molecules. In some embodiments, the library comprises at least two DNA molecules having different poly (A) tail coding sequences.

In addition, the present application also provides use of the above-mentioned engineered DNA molecule for stable amplifying the poly (A) tail coding sequence or the coding sequence of RNA with a poly (A) tail. In some embodiments, the method for amplifying the coding sequence of the poly (A) tail or the coding sequence of the RNA with the poly (A) tail is as described below in the method for stably amplifying the poly (A) tail transcription template DNA in vitro.

Engineered RNAs and Libraries

The present application provides an RNA comprising the aforementioned poly (A) tail and a gene of interest fragment on the 5' end side of the poly (A) tail coding sequence. In some embodiments, the RNA further comprises a 5'-cap structure. In some embodiments, the RNA is mRNA.

As used herein, "mRNA" (messenger RNA) is any RNA, naturally occurring, non-naturally occurring or modified, that encodes at least one protein, polypeptide, or a fragment thereof, which is enabled to be translated to produce the encoded protein, polypeptide, or a fragment thereof in vitro, in vivo, in situ, or ex vivo. Therefore, the mRNA may be a mature mRNA or a pre-mature mRNA, and the elements or structures that the mRNA must comprise or optionally comprise are known in the art. In some embodiments, the mRNA comprises coding sequences for multiple necessary functional elements to express, regulate, or enhance the expression level of the protein, polypeptide, or a fragment thereof. The functional elements include, but are not limited to, 5' cap, 5' UTR, 3' UTR, etc. Both the 5' UTR and the 3' UTR are usually transcribed from genomic DNA, which are the elements present in the pre-mature mRNA. As mature mRNA, The term "5' cap" is located at the 5' terminus of the mRNA, which comprises a methylated guanylate that is linked to the 5' terminus of the mRNA via pyrophosphate so as to form a 5',5'-triphosphate linkage with its adjacent nucleotide. There are usually three types of 5' cap structures (m7G5'ppp5'Np, m7G5'ppp5'NmpNp, and m7G5'ppp5'NmpNmpNp), which are called type O, type I and type II, respectively. The type O means that the ribose of the terminal nucleotide is not methylated, the type I means that the ribose of one terminal nucleotide is methylated, and the type II means that the ribose of both terminal nucleotides is methylated. In some embodiments, as for the 5' cap, according to the manufacturer's protocol, a 5'-guanosine cap structure can be produced by completion of capping the 5'of a polynucleotide during an in vitro transcription reaction through utilizing the following chemical RNA cap analogs: 3'-O-Me-m7G (5')ppp(5') G [ARCA cap], G (5')ppp(5') A, G (5')ppp(5') G, m7G (5')ppp(5') A, m7G (5')ppp(5') G (New England BioLabs, Ipswich, MA), or m7G (5')ppp(5') (2'-OMeA) pG (CleanCapAG®). For example, in some embodiments, 5' capping of the modified RNA can be accomplished after transcription by using vaccinia virus capping enzyme to produce an O-type cap structure: m7G (5')ppp(5') G (New England BioLabs, Ipswich, MA). The type I cap structures can be generated by using both vaccinia virus capping enzyme and 2'-O methyltransferase to produce m7G (5')ppp(5') (2'-OMeA) pG. The type II cap structures can be generated from the type I cap structures by subsequent 2'-O-methylation of the third nucleotide from 5'-terminus by using a 2'-O-methyl-transferase. The type III cap structures can be generated from the type II cap structures by subsequent 2'-O-methylation of the fourth nucleotide from 5'-terminus by using a 2'-O-methyltransferase.

In some embodiments, some or all of the uridines in the mRNA are chemically modified uridines.

In some embodiments, some or all of the uridines in the mRNA are pseudouridines or 1-methyl-pseudouridines.

In some embodiments, some or all of the uracil nucleotides in the mRNA are substituted with pseudouridine (ψ) nucleotides or N1-methyl-pseudouridine (m1ψ) nucleotides.

In some embodiments, the mRNA further comprises a stabilization element. The stabilization elements may comprise, for example, histone stem-loops. In some embodiments, the mRNA comprises a coding region, at least one histone stem-loop, and optionally a poly (A) sequence or a polyadenylation signal. The poly (A) sequence or polyadenylation signal should generally enhance the expression level of the encoded protein. In some embodiments, the mRNA comprises a combination of a poly (A) sequence or polyadenylation signal and at least one histone stem-loop, although both of them have alternative mechanisms in nature, they act synergistically to increase the protein expression to a level beyond those observed with either element alone. The synergistic effect of a combination of the poly (A) siand at least one histone stem-loop is independent of the order of the elements or the length of the poly (A) sisequence. In some embodiments, the histone stem-loop is generally derived from a histone gene, and comprises an intramolecular base-pairing formed loop by two adjacent partial or complete reverse complementary sequences separated by a spacer region (composed of a short sequence). The unpaired loop region is typically unable to base pair with either of the stem-loop elements. The stability of the stem-loop structure generally depends on the length, the number of mismatches or bulges, and the base composition of the paired region. In some embodiments, wobble base-pairing (non-Watson-Crick base-pairing) can be produced. In some embodiments, said at least one histone stem-loop sequence comprises 15-45 nucleotides in length.

In some embodiments, one or more AU-rich sequences of the mRNA may be removed. Such sequences are sometimes called AURES, which are destabilizing sequences found in the 3' UTR. The AURES may be removed from the mRNA. Alternatively, The AURES may be retained in the mRNA.

In some embodiments, the mRNA is formulated within a lipid nanoparticle (LNP). In some embodiments, lipids are mixed with the mRNA to form lipid nanoparticles. In some embodiments, the RNA is formulated in lipid nanoparticles.

In some embodiments, the lipid nanoparticles are first formed as empty lipid nanoparticles, and then are combined or encapsulated with the mRNA of the vaccine just prior to administration (e.g., within a few minutes to an hour).

The lipid nanoparticles generally comprise ionizable lipids, non-cationic lipids, sterols and PEG lipid components and a target nucleic acid, such as the above-mentioned mRNA. The lipid nanoparticles according to the present disclosure can be produced by using components, compositions and methods generally known in the art, see, e.g., PCT/US2016/052352, PCT/US2016/068300, PCT/US2017/037551, PCT/US2015/027400, PCT/US2016/047406, PCT/US2016000129, PCT/US2016/014280, PCT/US2016/014280, PCT/US2017/038426, PCT/US2014/027077, PCT/US2014/055394, PCT/US2016/52117, PCT/US2012/069610, PCT/US2017/027492, PCT/US2016/059575 and PCT/US2016/069491, all of which are incorporated herein by reference in their entireties.

The present application also provides a library comprising the aforementioned mRNA molecules. The library comprises at least two mRNA molecules with different poly (A) tails.

The present application also provides uses of the mRNA and the mRNA library. At least two or more mRNA molecules having poly (A) tails with different influence gradients on the expression level of mRNA can be used to regulate the expression level of the coding sequence of the aforementioned protein, polypeptide or a fragment thereof, for example, by adjusting the ratio of different mRNA molecules in the library comprising said two or more mRNA molecules, or by introducing one or more of said two or more mRNA molecules with the same or different contents at different times.

Cells

The present application also provides cells comprising the aforementioned engineered DNA molecules, wherein the DNA molecules can be stored and/or amplified in the cells. In some embodiments, the cells are prokaryotic cells in which the DNA molecules can be replicated. In some embodiments, the cells are prokaryotic cells in which the DNA molecules can be replicated and/or transcribed. In some embodiments, the DNA molecules are eukaryotic cells in which the DNA molecules can be replicated. In some embodiments, the DNA molecules can be transcribed and/or replicated in the DNA-containing cells.

In some embodiments, the cell is a prokaryotic cell. In some embodiments, the cell is a bacterium, an actinomycete, a cyanobacterium, a *mycoplasma*, a *rickettsia*, and a *chlamydia*. In some embodiments, the cell is selected from the group consisting of *Bacillus subtilis, Lactobacillus, Acetobacter, Corynebacterium, Brevibacterium, Arthrobacter, Pseudomonas*, and *Pediococcus*. In some embodiments, the cell is a recA-bacterium. In some embodiments, the cell is *E. coli*. In some embodiments, the cell is *E. coli*, which is selected from the group consisting of K-12 and derivatives thereof, and B strain and derivatives thereof. In some embodiments, the *E. coli* is selected from the group consisting of MG1655, DH5 or DH5a, DH10B, BL21, DB3.1™, HB101, JM109, JM110, MC1061, MG1655, Pir1, Stb12™, Stb13™, Top10, XL1Blue®, XL10Gold®, BLR, HMS174, Tuner™, Rostetta™2, Lemo21, T7Express, and Origami2™, etc. In some embodiments, the cell is selected from the group consisting of *Streptomyces, Micromonospora*, and *Nocardia*. In some embodiments, the cell is a fungus. In some embodiments, the cell is selected from a yeast or a mold.

Methods

The present application provides a method for stably amplifying a poly (A) tail transcription template DNA in vitro, so as to reduce the mutation frequency of the poly (A) tail transcription template sequence when the DNA is replicated in large quantities in a cell. The method comprises: expanding the cells comprising the engineered DNA molecules.

In some embodiments, prior to expanding the cells, the method further comprises introducing the engineered DNA molecule into the cells. In some embodiments, the introducing may comprise chemical transformation or electro-transformation. In some embodiments, the introducing is a natural endocytic process of the engineered DNA molecule performed by the cell.

In some embodiments, after expanding the cells, the method further comprises extracting cellular DNA and synthesizing the RNA by in vitro transcription. In some embodiments, after expanding the cells, the method further comprises inducing transcription of the RNA in the cells, and then extracting and isolating the RNA therein. In some embodiments, the method further comprises extracting the cellular DNA and transducing it into a second cell that can transcribe the RNA. In some embodiments, the transducing comprises administering to a human, wherein the administering is selected from the group consisting of intravenous, intraperitoneal, subcutaneous, intracranial, intrathecal, intraarterial (e.g., via the carotid artery), intramuscular, and intratumoral injection or perfusion.

In addition, the present application also provides a method for regulating protein expression, wherein the method comprises:

introducing two or more of the aforementioned engineered DNA molecules into cells of interest at different times and/or in different quantitative ratios; or introducing two or more of the aforementioned RNA molecules into cells of interest at different times and/or in different quantitative ratios;

wherein the two or more of the aforementioned engineered DNA molecules and the two or more of the aforementioned RNA molecules have different poly (A) tails, and the poly (A) tails have different influence gradients on the expression level of RNA.

In some embodiments, the present application also provides a method for regulating protein expression, wherein the method comprises introducing the aforementioned engineered DNA molecule or the aforementioned RNA molecule into a cell of interest. In some embodiments, the coding sequence of the poly (A) tail encoded by the DNA and the poly (A) tail comprised in the RNA comprises a structure selected from the group consisting of:

element a-element c-element b-element c-element b-element c-element b-element c-element b;

element b-element c-element b-element c-element a-element d-element b-element c-element b-element c-element b;

element b-element c-element b-element c-element b-element d-element a-element c;

element a-element d-element b-element c-element b-element c-element b; or element b-element c-element b-element c-element b-element d-element a.

In some embodiments, the coding sequence of the poly (A) tail encoded by the DNA and the poly (A) tail comprised in the RNA comprises a structure selected from the group consisting of:

60A-G-19A-G-19A-G-19A-G-3A;
7A-C-18A-G-60A-element d-7A-C-18A-G-14A;
60A-element d-19A-G-19A-G-17A;
19A-G-19A-G-19A-element d-60A;
19A-G-19A-G-19A-element d-60A-G;
19A-G-19A-G-19A-element d-60A;
19A-C-19A-C-19A-element d-60A; and
19A-T-19A-T-19A-element d-60A.

In some embodiments, the coding sequences of the poly (A) tail encoded by the DNA and the poly (A) tail comprised in the RNA comprise the following structure: 60A-element d-19A-G-19A-G-17A, or 19A-G-19A-G-19A-element d-60A.

Particularly, the two elements connected by the "-" are directly connected, and there is no nucleotide between the two elements.

In the above-mentioned structure of the poly (A) tail, "yA" represents the number of consecutive A in element a or element b, and y is a natural number, for example, 19A means that it comprises 19 consecutive A; 60A means that it comprises 60 consecutive A.

In some embodiments, the coding sequences of the poly (A) tail encoded by the DNA and the poly (A) tail comprised in the RNA comprise or consist of any one polynucleotide sequence selected from the polynucleotide sequences represented by SEQ ID NOs: 1-10.

It should be understood that the present application encompasses various aspects, embodiments and combinations of the aspects and/or embodiments described herein. The above description and the following Examples are intended to illustrate rather than limit the scope of the present application. Other aspects, improvements and modifications within the scope of the present application will be apparent to those skilled in the art. Therefore, those skilled in the art should appreciate that the scope of the present application also comprises such improvements and modifications to these aspects and embodiments.

EXAMPLES

Example 1: Construction of Poly (A) Tail

The poly (A) tails and the DNA sequences coding the poly (A) tails shown in Table 1 below were constructed by conventional genetic engineering methods.

TABLE 1

| Design | Specific structure | Sequence | Length |
|---|---|---|---|
| P1 | 60A-G-19A-G-19A-G-19A-G-AAA | SEQ ID NO: 1 | 124 nt |
| P2 | 7A-C-18A-G-60A-element d-7A-C-18A-G-14A | SEQ ID NO: 2 | 130 nt |
| P3 | 60A-element d-19A-G-19A-G-17A | SEQ ID NO: 3 | 123 nt |
| P4 | 19A-G-19A-G-19A- element d-60A | SEQ ID NO: 4 | 125 nt |
| P5 | 19A-G-19A-G-19A- element d-60A-G | SEQ ID NO: 5 | 126 nt |
| P6 | 19A-G-19A-G-19A-element d-60A | SEQ ID NO: 6 | 125 nt |
| P7 | 19A-G-19A-G-19A-element d-60A | SEQ ID NO: 7 | 131 nt |
| P8 | 19A-C-19A-C-19A-element d-60A | SEQ ID NO: 8 | 125 nt |
| P9 | 19A-T-19A-T-19A-element d-60A | SEQ ID NO: 9 | 125 nt |
| P10 | 19A-G-19A-G-19A-element d-60A | SEQ ID NO: 10 | 125 nt |
| C1 | A60-element d-A60 | SEQ ID NO: 11 | 130 nt |
| C2 | A30-element d-A70 | SEQ ID NO: 12 | 110 nt |
| C3 | A60-element c-A60 | SEQ ID NO: 13 | 121 nt |
| C4 | A60-element d-A60 | SEQ ID NO: 14 | 126 nt |

Example 2: Testing Poly (A) Function by Using Luciferase Coding Sequence as an Example 2.1 Testing the Replication Stability of mRNA-Encoding DNA Molecules in Prokaryotic Cells Using luciferase as the protein coding region, the stability of different poly (A) variants in *E. coli* and their effects on luciferase expression in cells were investigated.

1) Construction of a Universal Vector Comprising the Luciferase Protein Coding Region The *E. coli* cloning vector pUC57 was used as the vector backbone in this universal vector, and a T7 promoter sequence (SEQ ID NO: 27: 5'-TAATACGACTCACTATAAGG-3'), a 5' UTR, a luciferase protein, a 3' UTR and a polyadenylic acid string poly (dA:dT) were sequentially arranged between the multiple cloning sites: Xba I restriction site and the EcoR I restriction site.

2) The polyadenylic acid string poly (dA:dT) in the universal vector was substituted with P1-P10 of the present application, and controls $C_1$-$C_4$ (A60-10 nt spacer-A60 (control C1), A30-10 nt spacer-A70 (control C2), A60-1 nt spacer-A60 (control C3) or A60-6 nt spacer-A60 (control C4). Among them, the C1 and C2 are derived from a patent of the literature (U.S. Pat. No. U.S. Pat. No. 10,717,982B2).

All primers required for constructing P1-P10 and control $C_1$-$C_4$ were synthesized, and double digestion was conducted by two restriction endonucleases to remove the poly(dA:dT) from the universal vector constructed in step 1); and then P1-P10 and $C_1$-$C_4$ were ligated to the vector from which the poly(dA:dT) was removed by T4 DNA ligase 1, thereby completing the substitution of the poly(dA:dT) in the universal vector.

3) Detection of the Replication Stability of Different Poly (A) Variants in *E. coli*

The vector plasmid constructed in step 2) was confirmed to be correct by sequencing, and then transformed into *E. coli* DH5α. The transformed plate was grown at 30° C., then completing plasmid extraction and sequencing. After the sequencing was completed, the stability and base deletion of different poly (A) variants were analyzed and calculated based on the sequencing results. The replication stability is expressed by the percentage of clones without any base changes, and the higher the percentage, the higher the replication stability of the plasmid in *E. coli*.

Figure 2:
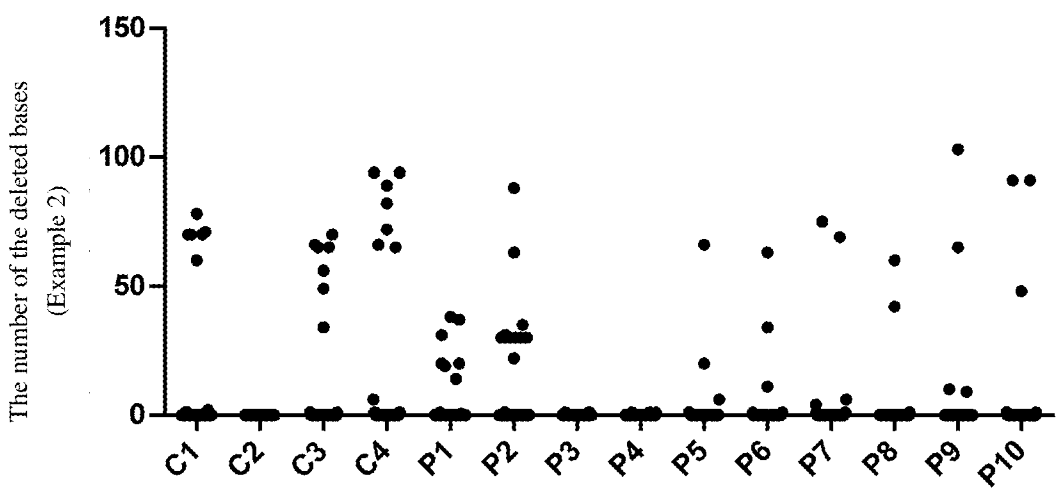
FIG. 2 shows the base deletion statistics of 10 poly (A) s in the present application in *E. coli* DH5a in Example 2.

The results are shown in FIGS. 1-2, and the specific experimental results are as follows:

A total of 100 clones were tested for control C1, in which 15 clones had base deletions, accounting for 15%; and the number of correct clones was 85, accounting for 85%.

A total of 50 clones were tested for control C2, in which all clones were correct without any base changes or deletions, with a correct clone percentage of 100%.

A total of 50 clones were tested for control C3, in which 9 clones had base deletions, accounting for 18%; and the number of correct clones was 41, accounting for 82%.

A total of 50 clones were tested for control C4, in which 14 clones had base deletions, accounting for 28%; and the number of correct clones was 36, accounting for 72%.

A total of 100 clones were tested for P1, in which 9 clones had base deletions, accounting for 9%; and the number of correct clones was 91, accounting for 91%.

A total of 100 clones were tested for P2, in which 12 clones had base deletions, accounting for 12%; the number of correct clones was 88, accounting for 88%.

A total of 62 clones were tested for P3, in which 5 clones had base deletions, accounting for 8%; and the number of correct clones was 57, accounting for 92%.

A total of 50 clones were tested for P4, in which 3 clones had base deletions, accounting for 6%; and the number of correct clones was 47, accounting for 94%.

A total of 50 clones were tested for P5, in which 4 clones had base deletions, accounting for 8%; and the number of correct clones was 46, accounting for 92%.

A total of 50 clones were tested for P6, in which 5 clones had base deletions, accounting for 10%; and the number of correct clones was 45, accounting for 90%.

A total of 50 clones were tested for P7, in which 7 clones had base deletions, accounting for 14%, and the number of correct clones was 43, accounting for 86%.

A total of 50 clones were tested for P8, in which 3 clones had base deletions, accounting for 6%, and the number of correct clones was 47, accounting for 94%.

A total of 50 clones were tested for P9, in which 4 clones had base deletions, accounting for 8%, and the number of correct clones was 46, accounting for 92%.

A total of 50 clones were tested for P10, in which 5 clones had base deletions, accounting for 10%, and the number of correct clones was 45, accounting for 90%.

Taking into account the results of the correct clone ratio and the number of deleted bases, the poly (A) variant designed in the present application is superior to or comparable to the prior art in terms of replication stability in *E. coli* cells. Particularly, the replication stability of poly (A) variants P3, P4, and P8 is the highest. The replication stability of P3, P4, and P8 is equivalent to that of C2, with no statistically significant difference ($p>0.05$, $\chi^2$ test). In addition, the replication stability of P3, P4, and P8 is better than that of the controls C1, C3 and C4, and the difference is statistically significant ($p<0.05$, $\chi^2$ test).

Example 3: Testing the Poly (A) Function by Using HPV Antigen Protein

Coding Sequence as an Example

1) Construction of Plasmid with HPV as Protein Coding Region

As described above, in Example 1, vectors comprising luciferase coding genes combined with different poly (A) s were constructed. Based on these vectors, the luciferase coding gene was substituted with the HPV coding gene by conventional molecular cloning methods; and the main elements were arranged in order of T7 promoter sequence (SEQ ID NO: 27: 5'-TAATACGACTCACTATAAGG-3'), 5' UTR, HPV antigen protein coding sequence, 3' UTR and poly (A) coding sequence.

2) Performing Small-Scale Bacterial Culture to Test the Stability of Four HPV Poly (A) Variants in *E. coli*

The HPV vector plasmid comprising P1, P2, P3 and P4 constructed in step 1) was confirmed to be correct by sequencing, and then transformed into *E. coli* DH5a. The transformed plates were grown at 30° C., then completing plasmid extraction and sequencing. After completion of sequencing, the stability and base deletion of different poly (A) variants were analyzed and calculated based on the sequencing results. The stability is expressed by the percentage of clones without any base changes, and the higher the percentage, the more stable it is.

Figure 3:
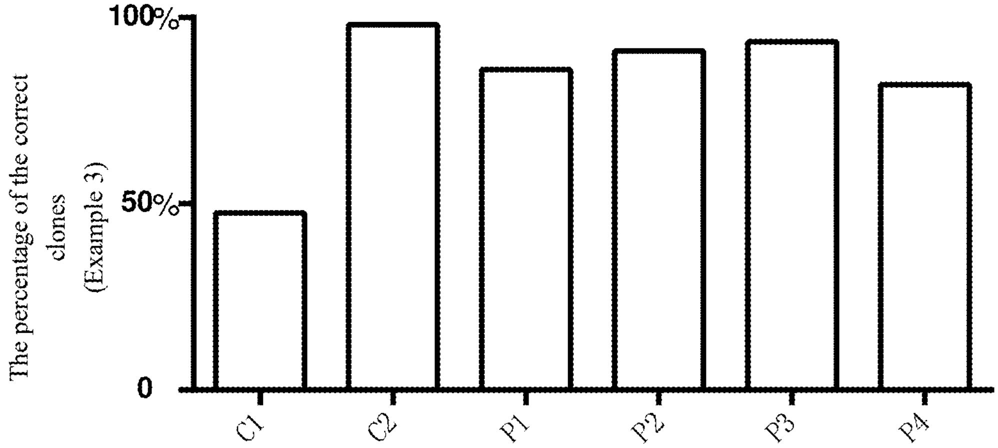
FIG. 3 shows the replication stability of poly (A) P1, P2, P3, P4 and poly (A) controls C1 and C2 in *E. coli* DH5a under a plasmid system comprising an HPV antigen sequences in Example 3.
Figure 4:
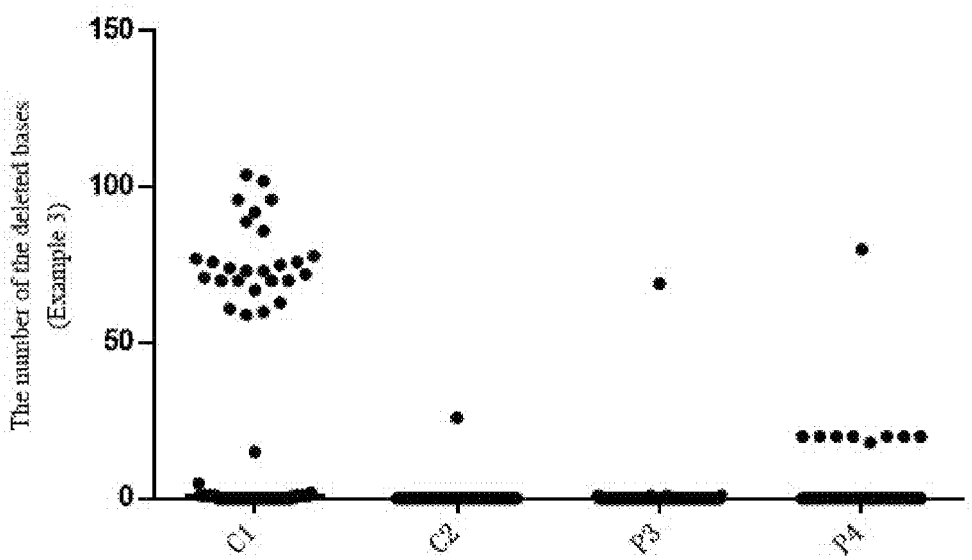
FIG. 4 shows the base deletion statistics of poly (A) P3, P4 and poly (A) controls C1 and C2 in *E. coli* DH5a under a plasmid system comprising an HPV antigen sequence in Example 3.

The results showed (FIGS. 3-4) that, when the gene of interest was substituted with the HPV antigen coding sequence,

- a total of 88 clones were tested for control C1, in which 47 clones had base deletions, accounting for 53%, and the number of correct clones was 41, accounting for 47%.
- a total of 50 clones were tested for control C2, in which 1 clone had a base deletion, accounting for 2%, and the number of correct clones was 49, accounting for 98%.
- a total of 101 clones were tested for P1, in which 14 clones had base deletions, accounting for 14%, and the number of correct clones was 87, accounting for 86%.
- a total of 100 clones were tested for P2, in which 12 clones had base deletions, accounting for 12%, and the number of correct clones was 88, accounting for 88%.
- a total of 70 clones were tested for P3, in which 4 clones had base deletions, accounting for 6%, and the number of correct clones was 66, accounting for 94%.
- a total of 50 clones were tested for P4, in which 9 clones had a plurality of base deletions, accounting for 18%, and the number of correct clones was 41, accounting for 82%.

Taking into account the ratio of mutations and the average number of base deletions, when the protein-coding gene of the luciferase in Example 1 was substituted with the HPV antigen protein, the different poly (A) variants of the present application still maintain high replication stability; particularly, P3 and C2 have comparable stability, with no statistically significant difference ($p>0.05$, $\chi^2$ test), and compared with new variants in other groups of the present application, the cloning stability is optimal. The probability of large fragment deletion in C2 is 1/50=2%, while the probability of large fragment deletion in P3 is 1/70=1.4%. Since large poly (A) fragment deletion will affect the in vivo expression and efficacy of mRNA products, P3 is more in line with product requirements. The above results indicate that the poly (A)

sivariants designed in the present application are universally applicable in examples involving different protein coding regions.

Figure 5:
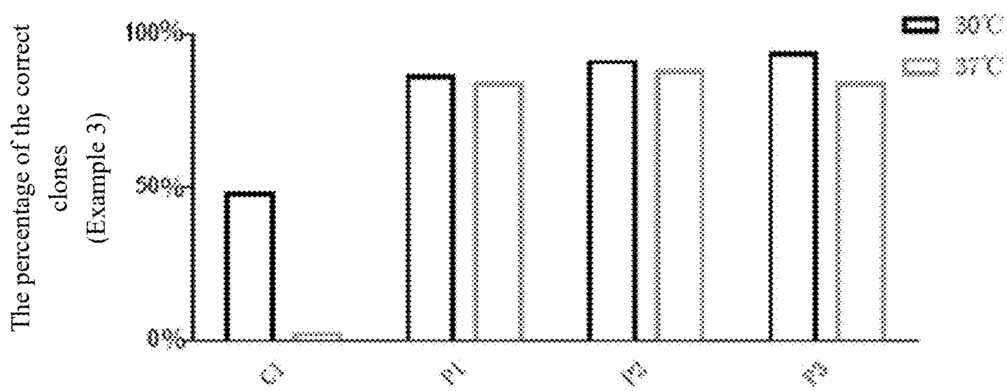
FIG. 5 shows the comparison of the replication stability between poly (A) P1, P2, P3 and poly (A) control C1 under two temperature conditions of 30° C. and 37° C. in *E. coli* DH5a in a plasmid system comprising an HPV antigen sequence in Example 3.
Figure 6:
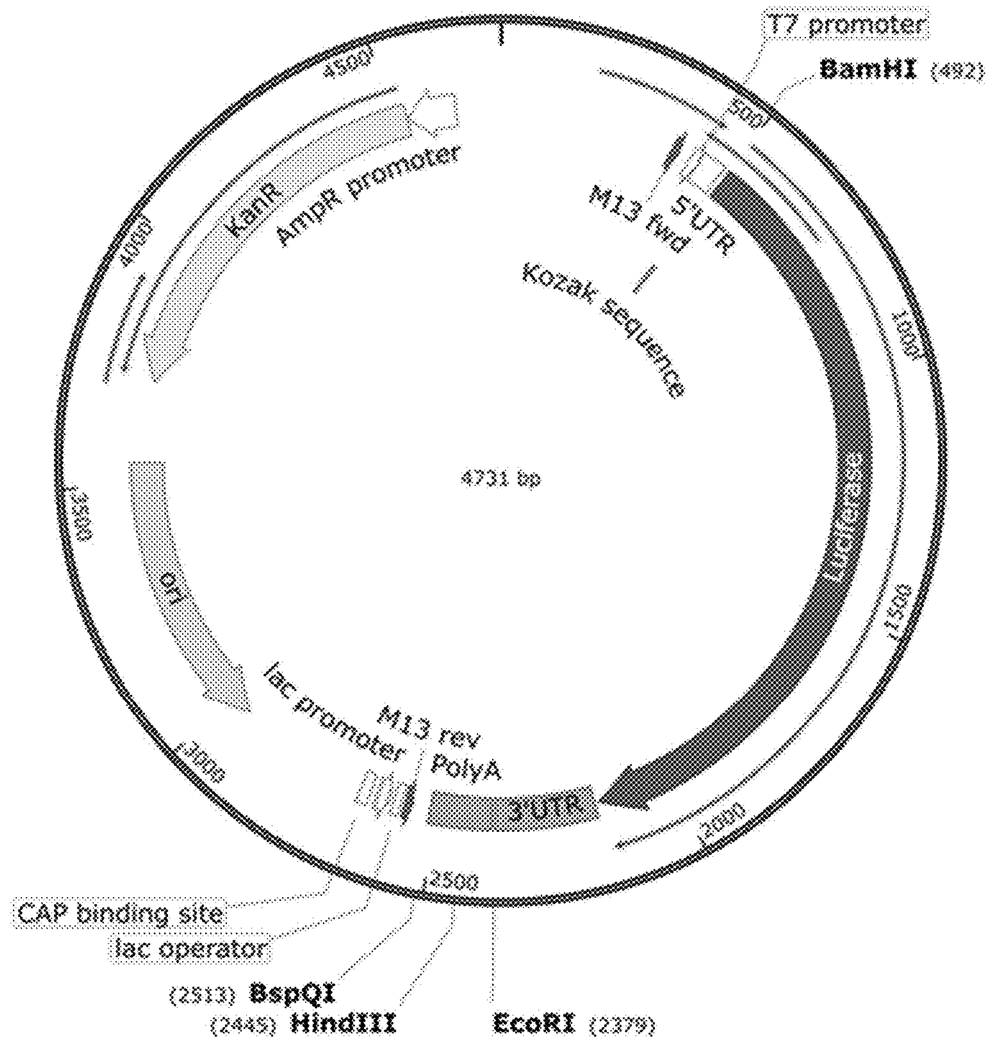
FIG. 6 shows an example of a universal vector plasmid DNA profile in the Examples.

As described above, in Example 1 and Example 2, the plates transformed with *E. coli* were cultured in a biochemical incubator at 30° C. overnight, and the obtained clones were sequenced to evaluate the replication stability. In addition, since the culture temperature of *E. coli* affects the DNA replication rate, which further affects the replication stability. With respect to Example 3, after the plates transformed with *E. coli* were cultured in a 37° C. biochemical incubator, the sequencing detections were also compared in the present application. The results show (FIG. 5) that, culturing at 37° C. significantly increases the base deletion ratio of the control C1, from 53% to 98% when culturing at 30° C. Unlike the control, there is no significant difference in the mutation rates of P1, P2 and P3 under the two temperature conditions, indicating that the poly (A) sivariants designed in the present application still have high replication stability in the examples with respect to different temperature culture conditions of *E. coli*, resulting in a universal application per se.

3) Detection of the Stability of the Three Poly (A) Variants in Large-Scale Fermentation and at Different Generations The production of mRNA drugs must rely on large-scale fermentation to prepare sufficient template plasmids, and the stability of the plasmid during fermentation (in this application, the stability of the plasmid particularly refers to the stability of poly dA:dT) is crucial to the production of mRNA drugs with uniform quality. On the other hand, in order to meet the stability requirements of different batches of production, it is necessary to establish a strain library comprising the plasmid of interest, including strain libraries of different generations such as primary library and secondary library. Therefore, it is necessary to evaluate the plasmid stability in *E. coli* for different generations. In response to the above two issues, the present application detected the stability of P1 and P3 between different generations of the fermentation process in Example 3. According to the sequencing results, 4 correct *E. coli* clones were selected for each poly (A) variant to perform passage culture through fermentation, respectively. The results show that, at the 3rd, 5th, 7th, and 9th seed passages, the plasmids of the four clones of P1 and P3 remain stable, without any base changes.

Example 4: Detection of Luciferase mRNA Expression Level in Mice

In eukaryotic cells, a poly (A) tail with a certain length is essential for protecting the 3' end of mRNA, maintaining mRNA stability and promoting protein expression. Affected by the physiological or environmental factors in the body, poly (A) gradually becomes shorter, thus priming mRNA degradation. This application investigated the effects of different poly (A) variants on protein expression levels. We performed in vivo expression assays in mice to evaluate the effects of different poly A variants on luciferase activity. During the implementation of this application, luciferase mRNA-LNP comprising control C2, as well as P3, P4, P5, P8 and P9 were injected intramuscularly into mice. Animal imaging was performed 6 hours after injection, and the fluorescence intensity was quantitatively to compare the effects of different poly (A) s on the activity of luciferase in vivo. The specific experimental process is as follows:

Luciferase mRNA was synthesized by in vitro transcription, and linearized DNA was obtained by digestion with type II restriction endonuclease BspQ I. The 3' end of the linearized DNA was exhibited as different poly (A): control C2, P3, P4, P5, P8 or P9. The linearized DNA was used as a template for in vitro transcription. A 100 μl reaction system in which 1X reaction buffer; 5 mM (final concentration) of ATP, CTP, NIM-UTP and GTP, respectively; 4 mM (final concentration) of CleanCap AG®; and 5 μl of in vitro transcriptase were included. After mixing the reaction mixture thoroughly, the reaction was conducted at 37° C. for 3 h. The in vitro transcribed mRNA was collected by LiCl precipitation, and finally dissolved in enzyme-free water.

Animal experiment: the in vitro synthesized luciferase mRNA was encapsulated into LNPs, and the obtained mRNA stock solution was dispersed in 20 mM acetic acid solution (pH 5.0) respectively to obtain an RNA solution with an mRNA concentration of 200 μg/mL. The mixed fat was prepared by mixing ionizable fat, cholesterol, DSPC, and DMG-PEG2000 with the molar ratio of ionizable fat: cholesterol:DSPC:DMG-PEG2000=50:38.5:10:1.5. The mRNA and the lipid mixture were mixed by controlling the flow rates of the aqueous phase and the oil phase through T mixing, and the injection pump was started to mix the mRNA solution with the lipid mixture to form LNP. Then, the solution was diluted 10 times with diluent, then concentrated by centrifugation in an ultrafiltration tube, followed by three times of replacement. The solution obtained above was added with Tris aqueous solution to adjust the pH to 7.0-8.0 to obtain an LNP-encapsulated mRNA solution, and the LNP means lipid nanoparticle. The concentration and particle size of the LNP-encapsulated mRNA were determined by using Ribogreen™ RNA quantification kit (Invitrogen, R11490) and Darwin ZetaSizer particle size analyzer, respectively. In the 4-component LNP, the molar ratio of each component is given as SM102:DSPC:cholesterol: DMG-PEG2000=50:10:38.5:1.5. After encapsulation, quality control was conducted for the LNP by measuring the particle size, encapsulation efficiency, PDI and other indicators. The quality control results show that the prepared LNPs meet the standards of particle size range of 50 nm-150 nm, PDI<0.3, and encapsulation efficiency>90%, which could be used for subsequent experiments. The mRNA content in LNP was determined by the Ribogreen™ method, and then LNP was diluted to an mRNA content of 100 ng/μL.

Figure 7:
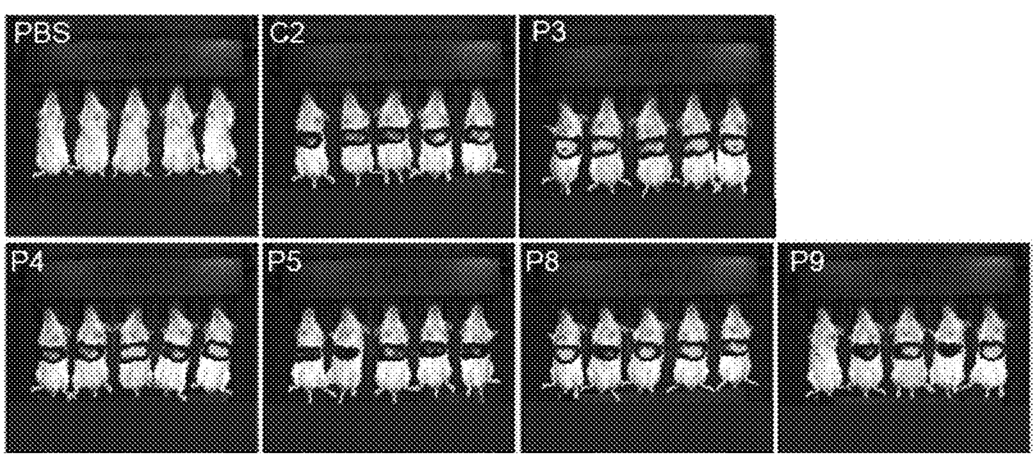
FIG. 7 shows the animal imaging results of the expression levels of luciferase with poly (A) P3, P4, P5, P8, P9 and control C2 in mice in Example 4.
Figure 8:
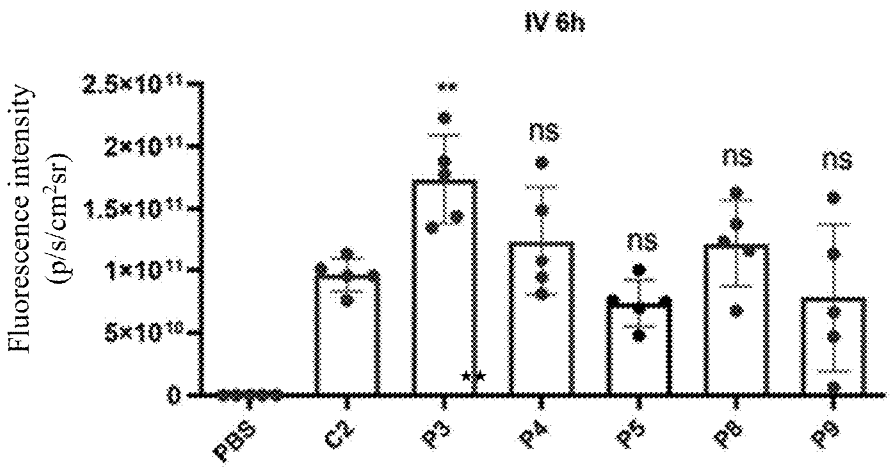
FIG. 8 shows the quantitative results of fluorescence intensity after animal imaging of the expression levels of luciferase with poly (A) P3, P4, P5, P8, P9 and control C2 in mice in Example 4 (ns, no significant difference; **, significant difference, $p<0.01$).

BALB/c mice were randomly divided into groups according to body weight, and administered after 2-3 days of adaptive feeding. Each of control C2, P3, P4, P5, P8 and P9 was respectively injected into five mice, and each mouse was administered 100 μl (10 μg mRNA) by intramuscular injection. In addition, five mice injected with PBS were used as a control group. Animal imaging was performed 6 h after the injection, and then fluorescence values were calculated. The results show (FIGS. 7-8) that, compared with the control C2, the expression activity of P3 is significantly increased by 1.8 times, with a statistically significant difference ($p<0.01$, student's t-test). The expression levels of P4, P5, P8 and P9 are comparable to that of C2, with no significant difference ($p>0.05$, student's t-test).

The sequences used in the above examples of this application are shown in the following sequence listing. It should be understood that, the following sequences are merely exemplary sequences of the embodiments of the present application, and do not impose any limitation on the embodiments of the present application. The nucleic acid sequences in the following sequence listing may represent DNA sequences or RNA sequences, and "T" represents a uridine when they represent RNA sequences.

| Sequence Listing: | | |
|---|---|---|
| SEQ ID NO. | Name | Sequence |
| | | Nucleic acid sequence |
| 1 | P1 | AAAAAAAAAAAAAAAAAAAAAAAAAAAAAAAAAAAAAA<br>AAAAAAAAAAAAAAAAAAAAAAGAAAAAAAAAAAAAAA<br>AAAAGAAAAAAAAAAAAAAAAAAAGAAAAAAAAAAAAA<br>AAAAAAGAAA |
| 2 | P2 | AAAAAAACAAAAAAAAAAAAAAAAAAGAAAAAAAAAAA<br>AAAAAAAAAAAAAAAAAAAAAAAAAAAAAAAAAAAAAA<br>AAAAAAAAAAAGGAAAAAAACAAAAAAAAAAAAAAAAA<br>AGAAAAAAAAAAAAAA |
| 3 | P3 | AAAAAAAAAAAAAAAAAAAAAAAAAAAAAAAAAAAAAA<br>AAAAAAAAAAAAAAAAAAAAAAGATATCAAAAAAAAAAA<br>AAAAAAAAGAAAAAAAAAAAAAAAAAAAGAAAAAAAAA<br>AAAAAAAA |
| 4 | P4 | AAAAAAAAAAAAAAAAAAAGAAAAAAAAAAAAAAAAAA<br>AGAAAAAAAAAAAAAAAAAAAGATATCAAAAAAAAAAAA<br>AAAAAAAAAAAAAAAAAAAAAAAAAAAAAAAAAAAAAA<br>AAAAAAAAAA |
| 5 | P5 | AAAAAAAAAAAAAAAAAAAGAAAAAAAAAAAAAAAAAA<br>AGAAAAAAAAAAAAAAAAAAAGATATCAAAAAAAAAAAA<br>AAAAAAAAAAAAAAAAAAAAAAAAAAAAAAAAAAAAAA<br>AAAAAAAAAAG |
| 6 | P6 | AAAAAAAAAAAAAAAAAAAGAAAAAAAAAAAAAAAAAA<br>AGAAAAAAAAAAAAAAAAAAAGTATACAAAAAAAAAAAA<br>AAAAAAAAAAAAAAAAAAAAAAAAAAAAAAAAAAAAAA<br>AAAAAAAAAA |
| 7 | P7 | AAAAAAAAAAAAAAAAAAAGAAAAAAAAAAAAAAAAAA<br>AGAAAAAAAAAAAAAAAAAAAGATATCGTATACAAAAAAA<br>AAAAAAAAAAAAAAAAAAAAAAAAAAAAAAAAAAAAAA<br>AAAAAAAAAAAAAAA |
| 8 | P8 | AAAAAAAAAAAAAAAAAAACAAAAAAAAAAAAAAAAAA<br>ACAAAAAAAAAAAAAAAAAAAGATATCAAAAAAAAAAAA<br>AAAAAAAAAAAAAAAAAAAAAAAAAAAAAAAAAAAAAA<br>AAAAAAAAAA |
| 9 | P9 | AAAAAAAAAAAAAAAAAAATAAAAAAAAAAAAAAAAAAA<br>TAAAAAAAAAAAAAAAAAAAGATATCAAAAAAAAAAAAA<br>AAAAAAAAAAAAAAAAAAAAAAAAAAAAAAAAAAAAAA<br>AAAAAAAAA |
| 10 | P10 | AAAAAAAAAAAAAAAAAAAGAAAAAAAAAAAAAAAAAA<br>AGAAAAAAAAAAAAAAAAAAAGAATCTAAAAAAAAAAAA<br>AAAAAAAAAAAAAAAAAAAAAAAAAAAAAAAAAAAAAA<br>AAAAAAAAAA |
| 11 | C1 | AAAAAAAAAAAAAAAAAAAAAAAAAAAAAAAAAAAAAA<br>AAAAAAAAAAAAAAAAAAAAAAGCATATGACTAAAAAAA<br>AAAAAAAAAAAAAAAAAAAAAAAAAAAAAAAAAAAAAA<br>AAAAAAAAAAAAAAA |
| 12 | C2 | AAAAAAAAAAAAAAAAAAAAAAAAAAAAAAGCATATGAC<br>TAAAAAAAAAAAAAAAAAAAAAAAAAAAAAAAAAAAAAA<br>AAAAAAAAAAAAAAAAAAAAAAAAAAAAAAAA |
| 13 | C3 | AAAAAAAAAAAAAAAAAAAAAAAAAAAAAAAAAAAAAA<br>AAAAAAAAAAAAAAAAAAAAAAGAAAAAAAAAAAAAAA<br>AAAAAAAAAAAAAAAAAAAAAAAAAAAAAAAAAAAAAA<br>AAAAAAA |
| 14 | C4 | AAAAAAAAAAAAAAAAAAAAAAAAAAAAAAAAAAAAAA<br>AAAAAAAAAAAAAAAAAAAAAAATGCATAAAAAAAAAAA<br>AAAAAAAAAAAAAAAAAAAAAAAAAAAAAAAAAAAAAA<br>AAAAAAAAAAA |

-continued

Sequence Listing:

| SEQ ID NO. | Name | Sequence |
|---|---|---|
| 15 | Element d, example 1 | GATATC |
| 16 | Element d, example 2 | GTATAC |
| 17 | Element d, example 3 | GAATCT |
| 18 | Element d, example 4 | GCATATGACT |
| 19 | Element d, example 5 | GATATCGTATAC |
| 20 | 3' UTR | CTCGCTTTCTTGCTGTCCAATTTCTATTAAAGGTTCCTTTGTT<br>CCCTAAGTCCAACTACTAAACTGGGGGATATTATGAAGGGC<br>CTTGAGCATCTGGATTCTGCCTGCTCGCTTTCTTGCTGTCCA<br>ATTTCTATTAAAGGTTCCTTTGTTCCCTAAGTCCAACTACTAA<br>ACTGGGGGATATTATGAAGGGCCTTGAGCATCTGGATTCTGC<br>CT |
| 21 | 5' UTR | ACATTTGCTTCTGACACAACTGTGTTCACTAGCAACCTCAA<br>ACAGACACC |
| 22 | Sequence of luciferase encoding gene | ATGGAAGACGCCAAAAACATTAAGAAGGGCCCAGCGCCAT<br>TCTACCCACTCGAAGACGGGACCGCCGGCGAGCAGCTGCA<br>CAAAGCCATGAAGCGCTACGCCCTGGTGCCCGGCACCATCG<br>CCTTTACCGACGCACATATCGAGGTGGACATTACCTACGCCG<br>AGTACTTCGAGATGAGCGTTCGGCTGGCAGAAGCTATGAAG<br>CGCTATGGGCTGAATACAAACCATCGGATCGTGGTGTGCAG<br>CGAGAATAGCTTGCAGTTCTTCATGCCCGTGTTGGGTGCCCT<br>GTTCATCGGTGTGGCTGTGGCCCCAGCTAACGACATCTACA<br>ACGAGCGCGAGCTGCTGAACAGCATGGGCATCAGCCAGCC<br>CACCGTCGTATTCGTGAGCAAGAAAGGGCTGCAAAAGATCC<br>TCAACGTGCAAAAGAAGCTACCGATCATACAAAAGATCATC<br>ATCATGGATAGCAAGACCGACTACCAGGGCTTCCAAAGCAT<br>GTACACCTTCGTGACTTCCCATTTGCCACCCGGCTTCAACG<br>AGTACGACTTCGTGCCCGAGAGCTTCGACCGGGACAAAAC<br>CATCGCCCTGATCATGAACAGTAGTGGCAGTACCGGATTGC<br>CCAAGGGCGTAGCCCTACCGCACCGCACCGCTTGTGTCCGA<br>TTCAGTCATGCCCGCGACCCCATCTTCGGCAACCAGATCATC<br>CCCGACACCGCTATCCTCAGCGTGGTGCCATTTCACCACGG<br>CTTCGGCATGTTCACCACGCTGGGCTACTTGATCTGCGGCTT<br>TCGGGTCGTGCTCATGTACCGCTTCGAGGAGGAGCTATTCTT<br>GCGCAGCTTGCAAGACTATAAGATTCAATCTGCCCTGCTGGT<br>GCCCACACTATTTAGCTTCTTCGCTAAGAGCACTCTCATCGA<br>CAAGTACGACCTAAGCAACTTGCACGAGATCGCCAGCGGC<br>GGGGCGCCGCTCAGCAAGGAGGTAGGTGAGGCCGTGGCCA<br>AACGCTTCCACCTACCAGGCATCCGCCAGGGCTACGGCCTG<br>ACAGAAACAACCAGCGCCATTCTGATCACCCCCGAAGGGG<br>ACGACAAGCCTGGCGCAGTAGGCAAGGTGGTGCCCTTCTTC<br>GAGGCTAAGGTGGTGGACTTGGACACCGGTAAGACACTGG<br>GTGTGAACCAGCGCGGCGAGCTGTGCGTCCGTGGCCCCATG<br>ATCATGAGCGGCTACGTTAACAACCCCGAGGCTACAAACGC<br>TCTCATCGACAAGGACGGCTGGCTGCACAGCGGCGACATCG<br>CCTACTGGGACGAGGACGAGCACTTCTTCATCGTGGACCGG<br>CTCAAAAGCCTGATCAAATACAAGGGCTACCAGGTAGCCCC<br>AGCCGAACTGGAGAGCATCCTGCTGCAACACCCCAACATCT<br>TCGACGCCGGGGTCGCCGGCCTGCCCGACGACGATGCCGG<br>CGAGCTGCCCGCCGCAGTCGTCGTGCTGGAACACGGTAAA<br>ACCATGACCGAGAAGGAGATCGTGGACTATGTGGCCAGCCA<br>GGTTACAACCGCCAAGAAGCTGCGCGGTGGTGTTGTGTTCG<br>TGGACGAGGTGCCTAAAGGACTGACCGGCAAGTTGGACGC<br>CCGCAAGATCCGCGAGATTCTCATTAAGGCCAAGAAGGGCG<br>GAAAGATCGCCGTGTAA |
| 23 | Sequence of HPV protein encoding gene | ATGGATGCTATGAAACGGGGCCTGTGCTGCGTGCTGCTCCT<br>GTGCGGCGCTGTGTTTGTGAGCCCTAGCATCACCCAGGACT<br>GCTCCTTCCAACACAGCCCCATCTCCTCCGACTTCGCTGTCA<br>AAATCCGTGAGCTGTCTGACTACCTGCTTCAAGATTACCCA<br>GTCACCGTGGCCTCCAACCTGCAGGACGAGGAGCTCTGCG<br>GGGGCCTCTGGCGGCTGGTCCTGGCACAGCGCTGGATGGA |

-continued

Sequence Listing:

| SEQ ID NO. | Name | Sequence |
|---|---|---|
| | | GCGGCTCAAGACTGTCGCTGGGTCCAAGATGCAAGGCTTGC<br>TGGAGCGCGTGAACACGGAGATACACTTTGTCACCAAATGT<br>GCCTTTCAGCCCCCCCCCAGCTGTCTTCGCTTCGTCCAGAC<br>CAACATCTCCCGCCTCCTGCAGGAGACCTCCGAGCAGCTGG<br>TGGCGCTGAAGCCCTGGATCACTCGCCAGAACTTCTCCCGG<br>TGCCTGGAGCTGCAGTGTCAGCCCGACTCCTCAACCCTGCC<br>ACCCCCATGGAGTCCCCGGCCCCTGGAGGCCACAGCCCCG<br>ACAGCCCCGGGCGGCGGCAGCGGCGATATGCACCAGAAGA<br>GAACCGCCATGTTCCAGGACCCTCAGGAGAGACCTAGGAA<br>GCTGCCTCACCTGTGTACAGAGCTCCAGACAACCATCCACG<br>ACATCATCCTGGAGTGCGTGTACTGTAAGCAGCAGCTGCTG<br>AGAAGAGAGGTGTACGACTTCGCCTTCAGAGACCTGTGCAT<br>CGTGTACAGAGACGGCAACCCTTACGCCGTGTGCGATAAGT<br>GTCTGAAGTTCTATTCCAAAATCTCCGAATATAGGTACATGC<br>ACGGCGACACCCCTACCCTGCACGAGTACATGCTGGACCTC<br>CAGCCTGAGACCACAGACCTGTACTGCTACGAGCAGCTGA<br>ACGACAGCTCTGAGGAAGAGGACGAGATTGACGGACCTGC<br>TGGCCAGGCCGAGCCTGACAGAGCCCACTACAATATCGTGA<br>CATTCTGTTGCAAATGCGACTCCACACTGGACAAGTGCCTG<br>AAGTTCTACAGCAAGATCTCTGAGTACAGATACTACTGCTAC<br>TCTGTGTACGGCACCACACTGGAGCAGCAGTACAACAAGC<br>CTCTGTGCGACCTCCTGATCCGCTGCATCAACTGCCAGAAG<br>CCTCTGTGCCCTGAGGAGAAGCAGAGACACCTGGACAAGA<br>AGCAGCGGTTCCACAACATCAGAGGCAGATGGACCGGCAG<br>GTGCATGTCCTGCTGTAGATCCTCCAGAACCAGACGGGAGA<br>CCCAGCTGCACTACAACATCGTGACCTTCTGCTGCAAGTGC<br>GACTCTACCCTGAGACTGTGCGTGCAGTCTACCCACGTGGA<br>CATCAGAACCCTGGAGGACCTGCTGATGGGCACCCTGGGCA<br>TCGTGTGCCCTATCTGCTCTCAGAAGCCTATGGCCAGGTTCG<br>AGGACCCTACCAGAAGACCCTACAAGCTGCCTGACCTGTGC<br>ACCGAGCTGAACACCTCTCTGCAAGACATCGAGATCACCTG<br>CGTGTACTGCAAGACCGTGCTGGAGCTGACCGAGGTGTTCG<br>AGTTCGCCTTCAAGGACCTGTTCGTGGTGTACAGAGACAGC<br>ATCCCTCACGCTGCCTGCCACAAGTGCATCGACTTCTATTCC<br>AGGATCAGGGAGCTGCGCTATTACTCCGACTCTGTGATGTAC<br>GGCCCCAAGGCCACCCTCCAGGACATCGTGCTGCACCTGGA<br>GCCTCAGAACGAGATCCCCGTGGACCTGCTGTGCCACGAGC<br>AGCTGTCTGACTCTGAAGAGGAGAACGACGAGATCGACGG<br>CGTGAACCACCAGCACCTGCCTGCCAGGAGAGCTGAACCC<br>CAGCGGCATACCATGCTGTGTATGTGCTTCTACTCTAGGATC<br>AGAGAGCTGAGGTACTACTCTGACTCTGTGTACGGCGACAC<br>CCTGGAGAAGCTGACCAACACCGGCCTGTACAACCTGCTGA<br>TCCGGTGCCTGAGGTGCCAGAAGCCTCTGAACCCTGCCGA<br>GAAGCTGAGACACCTGAACGAGAAGAGAAGATTCCACAAG<br>ATCGCTGGCCACTACAGAGGCCAGTGCCACTCTTGCTGCAA<br>CAGAGCCAGACAGGAGAGACTCCAGCGGAGAAGGGAGAC<br>CCAGGTGGCCAGGAGAGCCGAGCCTCAGAGACACACCATG<br>CTGTGCATGTGCTGCAAGTGCGAGGCCAGAATCGAGCTGGT<br>GGTGGAGAGCTCTGCCGACGACCTGAGAGCCTTCCAGCAG<br>CTGTTCCTGTCTACCCTGAGCTTCGTGTGCCCTTGGTGCGCC<br>TCTCAGCAGTAA |
| 24 | 5' UTR-HPV protein encoding gene-3' UTR-poly (A) P3 | ACATTTGCTTCTGACACAACTGTGTTCACTAGCAACCTCAA<br>ACAGACACCGGATCCGCCACCATGGATGCTATGAAACGGGG<br>CCTGTGCTGCGTGCTGCTCCTGTGCGGCGCTGTGTTTGTGA<br>GCCCTAGCATCACCCAGGACTGCTCCTTCCAACACAGCCCC<br>ATCTCCTCCGACTTCGCTGTCAAAATCCGTGAGCTGTCTGAC<br>TACCTGCTTCAAGATTACCCAGTCACCGTGGCCTCCAACCT<br>GCAGGACGAGGAGCTCTGCGGGGGCCTCTGGCGGCTGGTC<br>CTGGCACAGCGCTGGATGGAGCGGCTCAAGACTGTCGCTG<br>GGTCCAAGATGCAAGGCTTGCTGGAGCGCGTGAACACGGA<br>GATACACTTTGTCACCAAATGTGCCTTTCAGCCCCCCCCCAG<br>CTGTCTTCGCTTCGTCCAGACCAACATCTCCCGCCTCCTGCA<br>GGAGACCTCCGAGCAGCTGGTGGCGCTGAAGCCCTGGATC<br>ACTCGCCAGAACTTCTCCCGGTGCCTGGAGCTGCAGTGTCA<br>GCCCGACTCCTCAACCCTGCCACCCCCATGGAGTCCCCGGC<br>CCCTGGAGGCCACAGCCCCGACAGCCCCGGGCGGCGGCAG<br>CGGCGATATGCACCAGAAGAGAACCGCCATGTTCCAGGACC<br>CTCAGGAGAGACCTAGGAAGCTGCCTCACCTGTGTACAGA<br>GCTCCAGACAACCATCCACGACATCATCCTGGAGTGCGTGT<br>ACTGTAAGCAGCAGCTGCTGAGAAGAGAGGTGTACGACTT<br>CGCCTTCAGAGACCTGTGCATCGTGTACAGAGACGGCAACC<br>CTTACGCCGTGTGCGATAAGTGTCTGAAGTTCTATTCCAAAA |

-continued

Sequence Listing:

| SEQ ID NO. | Name | Sequence |
|---|---|---|
| | | TCTCCGAATATAGGTACATGCACGGCGACACCCCTACCCTGC ACGAGTACATGCTGGACCTCCAGCCTGAGACCACAGACCTG TACTGCTACGAGCAGCTGAACGACAGCTCTGAGGAAGAGG ACGAGATTGACGGACCTGCTGGCCAGGCCGAGCCTGACAG AGCCCACTACAATATCGTGACATTCTGTTGCAAATGCGACTC CACACTGGACAAGTGCCTGAAGTTCTACAGCAAGATCTCTG AGTACAGATACTACTGCTACTCTGTGTACGGCACCACACTG GAGCAGCAGTACAACAAGCCTCTGTGCGACCTCCTGATCCG CTGCATCAACTGCCAGAAGCCTCTGTGCCCTGAGGAGAAGC AGAGACACCTGGACAAGAAGCAGCGGTTCCACAACATCAG AGGCAGATGGACCGGCAGGTGCATGTCCTGCTGTAGATCCT CCAGAACCAGACGGGAGACCCAGCTGCACTACAACATCGT GACCTTCTGCTGCAAGTGCGACTCTACCCTGAGACTGTGCG TGCAGTCTACCCACGTGGACATCAGAACCCTGGAGGACCTG CTGATGGGCACCCTGGGCATCGTGTGCCCTATCTGCTCTCAG AAGCCTATGGCCAGGTTCGAGGACCCTACCAGAAGACCCTA CAAGCTGCCTGACCTGTGCACCGAGCTGAACACCTCTCTGC AAGACATCGAGATCACCTGCGTGTACTGCAAGACCGTGCTG GAGCTGACCGAGGTGTTCGAGTTCGCCTTCAAGGACCTGTT CGTGGTGTACAGAGACAGCATCCCTCACGCTGCCTGCCACA AGTGCATCGACTTCTATTCCAGGATCAGGGAGCTGCGCTATT ACTCCGACTCTGTGATGTACGGCCCCAAGGCCACCCTCCAG GACATCGTGCTGCACCTGGAGCCTCAGAACGAGATCCCCGT GGACCTGCTGTGCCACGAGCAGCTGTCTGACTCTGAAGAG GAGAACGACGAGATCGACGGCGTGAACCACCAGCACCTGC CTGCCAGGAGAGCTGAACCCCAGCGGCATACCATGCTGTGT ATGTGCTTCTACTCTAGGATCAGAGAGCTGAGGTACTACTCT GACTCTGTGTACGGCGACACCCTGGAGAAGCTGACCAACA CCGGCCTGTACAACCTGCTGATCCGGTGCCTGAGGTGCCAG AAGCCTCTGAACCCTGCCGAGAAGCTGAGACACCTGAACG AGAAGAGAAGATTCCACAAGATCGCTGGCCACTACAGAGG CCAGTGCCACTCTTGCTGCAACAGAGCCAGACAGGAGAGA CTCCAGCGGAGAAGGGAGACCCAGGTGGCCAGGAGAGCC GAGCCTCAGAGACACACCATGCTGTGCATGTGCTGCAAGTG CGAGGCCAGAATCGAGCTGGTGGTGGAGAGCTCTGCCGAC GACCTGAGAGCCTTCCAGCAGCTGTTCCTGTCTACCCTGAG CTTCGTGTGCCCTTGGTGCGCCTCTCAGCAGTAAGGCGCGC CGCTCGCTTTCTTGCTGTCCAATTTCTATTAAAGGTTCCTTTG TTCCCTAAGTCCAACTACTAAACTGGGGGATATTATGAAGGG CCTTGAGCATCTGGATTCTGCCTGCTCGCTTTCTTGCTGTCC AATTTCTATTAAAGGTTCCTTTGTTCCCTAAGTCCAACTACTA AACTGGGGGATATTATGAAGGGCCTTGAGCATCTGGATTCTG CCTGAATTCAAAAAAAAAAAAAAAAAAAAAAAAAAAAAA AAAAAAAAAAAAAAAAAAAAAAAAAAAAAAGATATCAAA AAAAAAAAAAAAAAAAGAAAAAAAAAAAAAAAAAAAGA AAAAAAAAAAAAAAAA |
| 25 | 5' UTR-HPV protein encoding gene-3' UTR-poly (A) P4 | ACATTTGCTTCTGACACAACTGTGTTCACTAGCAACCTCAA ACAGACACCGGATCCGCCACCATGGATGCTATGAAACGGGG CCTGTGCTGCGTGCTGCTCCTGTGCGGCGCTGTGTTTGTGA GCCCTAGCATCACCCAGGACTGCTCCTTCCAACACAGCCCC ATCTCCTCCGACTTCGCTGTCAAAATCCGTGAGCTGTCTGAC TACCTGCTTCAAGATTACCCAGTCACCGTGGCCTCCAACCT GCAGGACGAGGAGCTCTGCGGGGGCCTCTGGCGGCTGGTC CTGGCACAGCGCTGGATGGAGCGGCTCAAGACTGTCGCTG GGTCCAAGATGCAAGGCTTGCTGGAGCGCGTGAACACGGA GATACACTTTGTCACCAAATGTGCCTTTCAGCCCCCCCCAG CTGTCTTCGCTTCGTCCAGACCAACATCTCCCGCCTCCTGCA GGAGACCTCCGAGCAGCTGGTGGCGCTGAAGCCCTGGATC ACTCGCCAGAACTTCTCCCGGTGCCTGGAGCTGCAGTGTCA GCCCGACTCCTCAACCCTGCCACCCCCATGGAGTCCCCGGC CCCTGGAGGCCACAGCCCCGACAGCCCCGGGCGGCGGCAG CGGCGATATGCACCAGAAGAGAACCGCCATGTTCCAGGACC CTCAGGAGAGACCTAGGAAGCTGCCTCACCTGTGTACAGA GCTCCAGACAACCATCCACGACATCATCCTGGAGTGCGTGT ACTGTAAGCAGCAGCTGCTGAGAAGAGAGGTGTACGACTT CGCCTTCAGAGACCTGTGCATCGTGTACAGAGACGGCAACC CTTACGCCGTGTGCGATAAGTGTCTGAAGTTCTATTCCAAAA TCTCCGAATATAGGTACATGCACGGCGACACCCCTACCCTGC ACGAGTACATGCTGGACCTCCAGCCTGAGACCACAGACCTG TACTGCTACGAGCAGCTGAACGACAGCTCTGAGGAAGAGG ACGAGATTGACGGACCTGCTGGCCAGGCCGAGCCTGACAG AGCCCACTACAATATCGTGACATTCTGTTGCAAATGCGACTC |

-continued

Sequence Listing:

| SEQ ID NO. | Name | Sequence |
|---|---|---|
| | | CACACTGGACAAGTGCCTGAAGTTCTACAGCAAGATCTCTG<br>AGTACAGATACTACTGCTACTCTGTGTACGGCACCACACTG<br>GAGCAGCAGTACAACAAGCCTCTGTGCGACCTCCTGATCCG<br>CTGCATCAACTGCCAGAAGCCTCTGTGCCCTGAGGAGAAGC<br>AGAGACACCTGGACAAGAAGCAGCGGTTCCACAACATCAG<br>AGGCAGATGGACCGGCAGGTGCATGTCCTGCTGTAGATCCT<br>CCAGAACCAGACGGGAGACCCAGCTGCACTACAACATCGT<br>GACCTTCTGCTGCAAGTGCGACTCTACCCTGAGACTGTGCG<br>TGCAGTCTACCCACGTGGACATCAGAACCCTGGAGGACCTG<br>CTGATGGGCACCCTGGGCATCGTGTGCCCTATCTGCTCTCAG<br>AAGCCTATGGCCAGGTTCGAGGACCCTACCAGAAGACCCTA<br>CAAGCTGCCTGACCTGTGCACCGAGCTGAACACCTCTCTGC<br>AAGACATCGAGATCACCTGCGTGTACTGCAAGACCGTGCTG<br>GAGCTGACCGAGGTGTTCGAGTTCGCCTTCAAGGACCTGTT<br>CGTGGTGTACAGAGACAGCATCCCTCACGCTGCCTGCCACA<br>AGTGCATCGACTTCTATTCCAGGATCAGGGAGCTGCGCTATT<br>ACTCCGACTCTGTGATGTACGGCCCCAAGGCCACCCTCCAG<br>GACATCGTGCTGCACCTGGAGCCTCAGAACGAGATCCCCGT<br>GGACCTGCTGTGCCACGAGCAGCTGTCTGACTCTGAAGAG<br>GAGAACGACGAGATCGACGGCGTGAACCACCAGCACCTGC<br>CTGCCAGGAGAGCTGAACCCCAGCGGCATACCATGCTGTGT<br>ATGTGCTTCTACTCTAGGATCAGAGAGCTGAGGTACTACTCT<br>GACTCTGTGTACGGCGACACCCTGGAGAAGCTGACCAACA<br>CCGGCCTGTACAACCTGCTGATCCGGTGCCTGAGGTGCCAG<br>AAGCCTCTGAACCCTGCCGAGAAGCTGAGACACCTGAACG<br>AGAAGAGAAGATTCCACAAGATCGCTGGCCACTACAGAGG<br>CCAGTGCCACTCTTGCTGCAACAGAGCCAGACAGGAGAGA<br>CTCCAGCGGAGAAGGGAGACCCAGGTGGCCAGGAGAGCC<br>GAGCCTCAGAGACACACCATGCTGTGCATGTGCTGCAAGTG<br>CGAGGCCAGAATCGAGCTGGTGGTGGAGAGCTCTGCCGAC<br>GACCTGAGAGCCTTCCAGCAGCTGTTCCTGTCTACCCTGAG<br>CTTCGTGTGCCCTTGGTGCGCCTCTCAGCAGTAAGGCGCGC<br>CGCTCGCTTTCTTGCTGTCCAATTTCTATTAAAGGTTCCTTTG<br>TTCCCTAAGTCCAACTACTAAACTGGGGGATATTATGAAGGG<br>CCTTGAGCATCTGGATTCTGCCTGCTCGCTTTCTTGCTGTCC<br>AATTTCTATTAAAGGTTCCTTTGTTCCCTAAGTCCAACTACTA<br>AACTGGGGGATATTATGAAGGGCCTTGAGCATCTGGATTCTG<br>CCTGAATTCAAAAAAAAAAAAAAAAAAAGAAAAAAAAAA<br>AAAAAAAAAGAAAAAAAAAAAAAAAAAAGATATCAAAA<br>AAAAAAAAAAAAAAAAAAAAAAAAAAAAAAAAAAAAAA<br>AAAAAAAAAAAAAAAAAA |
| 26 | Sequence of HPV protein | MDAMKRGLCCVLLLCGAVFVSPSITQDCSFQHSPISSDFAVKIR<br>ELSDYLLQDYPVTVASNLQDEELCGGLWRLVLAQRWMERLK<br>TVAGSKMQGLLERVNTEIHFVTKCAFQPPPSCLRFVQTNISRLL<br>QETSEQLVALKPWITRQNFSRCLELQCQPDSSTLPPPWSPRPLE<br>ATAPTAPGGGSGDMHQKRTAMFQDPQERPRKLPHLCTELQTTI<br>HDIILECVYCKQQLLRREVYDFAFRDLCIVYRDGNPYAVCDKC<br>LKFYSKISEYRYMHGDTPTLHEYMLDLQPETTDLYCYEQLND<br>SSEEEDEIDGPAGQAEPDRAHYNIVTFCCKCDSTLDKCLKFYS<br>KISEYRYYCYSVYGTTLEQQYNKPLCDLLIRCINCQKPLCPEE<br>KQRHLDKKQRFHNIRGRWTGRCMSCCRSSRTRRETQLHYNIV<br>TFCCKCDSTLRLCVQSTHVDIRTLEDLLMGTLGIVCPICSQKP<br>MARFEDPTRRPYKLPDLCTELNTSLQDIEITCVYCKTVLELTE<br>VFEFAFKDLFVVYRDSIPHAACHKCIDFYSRIRELRYYSDSVM<br>YGPKATLQDIVLHLEPQNEIPVDLLCHEQLSDSEEENDEIDGV<br>NHQHLPARRAEPQRHTMLCMCFYSRIRELRYYSDSVYGDTLE<br>KLTNTGLYNLLIRCLRCQKPLNPAEKLRHLNEKRRFHKIAGHY<br>RGQCHSCCNRARQERLQRRRETQVARRAEPQRHTMLCMCCK<br>CEARIELVVESSADDLRAFQQLFLSTLSFVCPWCASQQ |

The invention claimed is:

1. An engineered DNA molecule capable of being replicated in a cell, comprising a polyadenosine tail (Poly A tail) coding sequence, wherein the poly (A) tail coding sequence comprises: a single element a and at least one element b, and at least one element c and at least one element d:

the element a consists of a plurality of consecutive adenine (A) nucleotides, and the length range of the element a is ≥20 nt and <80 nt;

the element b consists of a plurality of consecutive A nucleotides, and the length range of the element b is 3 nt≤b<20 nt;

the element c consists of a non-A nucleotide, and the nucleotide is selected from T, C and G nucleotides;

the element d consists of any two or more consecutive nucleotides, and the nucleotides are selected from A, T, C and G nucleotides, wherein the nucleotides at a 5' terminus and a 3' terminus of the element d are not A nucleotides, and the element d does not comprise 3 or more consecutive A nucleotides; the length range of the element d is 2 nt≤d≤20 nt; and the element d comprises a palindromic sequence;

wherein the element a and the element b are not adjacent, and the element c and the element d are not adjacent, and the poly (A) tail coding sequence does not comprise any two elements b that are adjacent to each other, does not comprise any two elements c that are adjacent to each other, and does not comprise any two elements d that are adjacent to each other.

2. The DNA molecule according to claim 1, wherein the length of the poly (A) tail coding sequence is 101-200 nt.

3. The DNA molecule according to claim 1, wherein the 3' terminus of the poly (A) tail coding sequence is an A nucleotide or a non-A nucleotide.

4. The DNA molecule according to claim 1, wherein 50% or more of the polynucleotides of element a are located in the 5' portion or 3' portion of the poly (A) tail coding sequence.

5. The DNA molecule according to claim 1, wherein the element c is G.

6. The DNA molecule according to claim 1, wherein the element d is any one or more selected from the following sequences: GATATC and GTATAC.

7. The DNA molecule according to claim 1, wherein the number of the element d is 1-5.

8. The DNA molecule according to claim 1, wherein the total number of the element c and the element d is 2-15.

9. The DNA molecule according to claim 1, wherein the 3' portion of the poly (A) tail coding sequence comprises one or more non-A nucleotides.

10. The DNA molecule according to claim 1, wherein the structure of the poly (A) tail coding sequence is:

element a-element d-element b-element c-element b-element c-element b.

11. The DNA molecule according to claim 1, wherein the poly (A) tail coding sequence is represented by SEQ ID NO: 3.

12. The DNA molecule according to claim 1, wherein it is further connected to a gene of interest fragment on the 5' end of the poly (A) tail coding sequence, and the gene of interest fragment and the poly (A) tail coding sequence co-encode RNA.

13. The DNA molecule according to claim 12, further comprising a replicon, a resistance gene, and/or a promoter for initiating transcription of the RNA.

14. The DNA molecule according to claim 12, wherein the gene of interest fragment comprises a 5' UTR coding sequence, and/or a 3' UTR coding sequence.

15. The DNA molecule according to claim 12, wherein the gene of interest fragment comprises a protein coding sequence or a non-protein coding sequence.

16. The DNA molecule according to claim 12, comprising a replicon, an antibiotic resistance gene, a promoter, a 5' UTR coding sequence, a protein coding sequence, and a 3' UTR coding sequence.

17. The DNA molecule according to claim 1, comprising a polynucleotide sequence represented by any one of SEQ ID NOs: 22-24, or a synonymous mutant of the polynucleotide sequence represented by any one of SEQ ID NOs: 22-24, or a polynucleotide sequence sharing more than 85% sequence identity with the polynucleotide sequence represented by any one of SEQ ID NOs: 22-24 or a synonymous mutant thereof.

18. A cell comprising the DNA molecule according to claim 1, wherein the cell is a prokaryotic cell.

19. A library comprising the DNA molecule according to claim 1.

20. A method for regulating protein expression, comprising:

introducing a plurality of DNAs in the library according to claim 19 into target cells at different times and/or in different quantitative ratios.

21. A hybrid molecule of DNA and RNA, comprising the same genetic information as the DNA molecule according to claim 1.

22. An engineered DNA molecule capable of being replicated in a cell, comprising a polyadenosine tail (Poly A tail) coding sequence, wherein the structure of the poly (A) tail coding sequence is:

1) Element a-element d-element b-element c-element b-element c-element b; the element a is 60 nt in length, the element b is 16-19 nt in length, and the element d is 6 nt in length, or 2) Element b-element c-element b-element c-element b-element d-element a; and the element a is 60 nt in length, the element b is 16-19 nt in length, and the element d is 6 nt in length;

wherein the element a consists of a plurality of consecutive adenine (A) nucleotides;

the element b consists of a plurality of consecutive A nucleotides;

the element c consists of a non-A nucleotide, and the nucleotide is selected from T, C and G nucleotides; and the element d consists of any two or more consecutive nucleotides, and the nucleotides are selected from A, T, C and G nucleotides, wherein the nucleotides at a 5' terminus and a 3' terminus of the element d are not A nucleotides, and the element d does not comprise 3 or more consecutive A nucleotides.

23. An RNA molecule encoded by an engineered DNA molecule capable of being replicated in a cell, wherein the engineered DNA molecule comprises a polyadenosine tail (Poly A tail) coding sequence, wherein the poly (A) tail coding sequence comprises: a single element a and at least one element b, and at least one element c and at least one element d:

the element a consists of a plurality of consecutive adenine (A) nucleotides, and the length range of the element a is ≥20 nt and <80 nt;

the element b consists of a plurality of consecutive A nucleotides, and the length range of the element b is 3 nt≤b<20 nt;

the element c consists of a non-A nucleotide, and the nucleotide is selected from T, C and G nucleotides;

the element d consists of any two or more consecutive nucleotides, and the nucleotides are selected from A, T, C and G nucleotides, wherein the nucleotides at a 5' terminus and a 3' terminus of the element d are not A nucleotides, the element d does not comprise 3 or more consecutive A nucleotides; and the length range of the element d is 2 nt≤d≤20 nt; and the element d comprises a palindromic sequence;

wherein the element a and the element b are not adjacent, and the element c and the element d are not adjacent, and the poly (A) tail coding sequence does not comprise any two elements b that are adjacent to each other, does not comprise any two elements c that are adjacent to each other, and does not comprise any two elements d that are adjacent to each other.

24. The RNA molecule according to claim 23, further comprising a 5'-cap structure, and/or some or all of the uridines in the RNA are chemically modified uridines.

25. A library comprising the RNA molecule according to claim 23.

* * * * *

SEQUENCE LISTING

Sequence total quantity: 27
SEQ ID NO: 1 moltype = DNA length = 124
FEATURE Location/Qualifiers
source 1..124
mol_type = other DNA
organism = synthetic construct -continued

```
SEQUENCE: 1
aaaaaaaaaa aaaaaaaaaa aaaaaaaaaa aaaaaaaaaa aaaaaaaaaa aaaaaaaaaa  60
gaaaaaaaaa aaaaaaaaaa gaaaaaaaaa aaaaaaaaaa gaaaaaaaaa aaaaaaaaaa  120
gaaa                                                               124

SEQ ID NO: 2            moltype = DNA  length = 130
FEATURE                 Location/Qualifiers
source                  1..130
                        mol_type = other DNA
                        organism = synthetic construct
SEQUENCE: 2
aaaaaaacaa aaaaaaaaaa aaaaaagaaa aaaaaaaaaa aaaaaaaaaa aaaaaaaaaa  60
aaaaaaaaaa aaaaaaaaaa aaaaaaagga aaaaaacaaa aaaaaaaaaa aaaaagaaaa  120
aaaaaaaaaa                                                         130

SEQ ID NO: 3            moltype = DNA  length = 123
FEATURE                 Location/Qualifiers
source                  1..123
                        mol_type = other DNA
                        organism = synthetic construct
SEQUENCE: 3
aaaaaaaaaa aaaaaaaaaa aaaaaaaaaa aaaaaaaaaa aaaaaaaaaa aaaaaaaaaa  60
gatatcaaaa aaaaaaaaaa aaaaagaaaa aaaaaaaaaa aaaaagaaaa aaaaaaaaaa  120
aaa                                                                123

SEQ ID NO: 4            moltype = DNA  length = 125
FEATURE                 Location/Qualifiers
source                  1..125
                        mol_type = other DNA
                        organism = synthetic construct
SEQUENCE: 4
aaaaaaaaaa aaaaaaaaag aaaaaaaaaa aaaaaaaaag aaaaaaaaaa aaaaaaaaag  60
atatcaaaaa aaaaaaaaaa aaaaaaaaaa aaaaaaaaaa aaaaaaaaaa aaaaaaaaaa  120
aaaaa                                                              125

SEQ ID NO: 5            moltype = DNA  length = 126
FEATURE                 Location/Qualifiers
source                  1..126
                        mol_type = other DNA
                        organism = synthetic construct
SEQUENCE: 5
aaaaaaaaaa aaaaaaaaag aaaaaaaaaa aaaaaaaaag aaaaaaaaaa aaaaaaaaag  60
atatcaaaaa aaaaaaaaaa aaaaaaaaaa aaaaaaaaaa aaaaaaaaaa aaaaaaaaaa  120
aaaaag                                                             126

SEQ ID NO: 6            moltype = DNA  length = 125
FEATURE                 Location/Qualifiers
source                  1..125
                        mol_type = other DNA
                        organism = synthetic construct
SEQUENCE: 6
aaaaaaaaaa aaaaaaaaag aaaaaaaaaa aaaaaaaaag aaaaaaaaaa aaaaaaaaag  60
tatacaaaaa aaaaaaaaaa aaaaaaaaaa aaaaaaaaaa aaaaaaaaaa aaaaaaaaaa  120
aaaaa                                                              125

SEQ ID NO: 7            moltype = DNA  length = 131
FEATURE                 Location/Qualifiers
source                  1..131
                        mol_type = other DNA
                        organism = synthetic construct
SEQUENCE: 7
aaaaaaaaaa aaaaaaaaag aaaaaaaaaa aaaaaaaaag aaaaaaaaaa aaaaaaaaag  60
atatcgtata caaaaaaaaa aaaaaaaaaa aaaaaaaaaa aaaaaaaaaa aaaaaaaaaa  120
aaaaaaaaaa a                                                       131

SEQ ID NO: 8            moltype = DNA  length = 125
FEATURE                 Location/Qualifiers
source                  1..125
                        mol_type = other DNA
                        organism = synthetic construct
SEQUENCE: 8
aaaaaaaaaa aaaaaaaaac aaaaaaaaaa aaaaaaaaac aaaaaaaaaa aaaaaaaaag  60
atatcaaaaa aaaaaaaaaa aaaaaaaaaa aaaaaaaaaa aaaaaaaaaa aaaaaaaaaa  120
aaaaa                                                              125

SEQ ID NO: 9            moltype = DNA  length = 125
FEATURE                 Location/Qualifiers
source                  1..125
                        mol_type = other DNA
```

-continued

```
                         organism = synthetic construct
SEQUENCE: 9
aaaaaaaaaa aaaaaaaaat aaaaaaaaaa aaaaaaaaat aaaaaaaaaa aaaaaaaaag  60
atatcaaaaa aaaaaaaaaa aaaaaaaaaa aaaaaaaaaa aaaaaaaaaa aaaaaaaaaa  120
aaaaa                                                              125

SEQ ID NO: 10            moltype = DNA  length = 125
FEATURE                  Location/Qualifiers
source                   1..125
                         mol_type = other DNA
                         organism = synthetic construct
SEQUENCE: 10
aaaaaaaaaa aaaaaaaaag aaaaaaaaaa aaaaaaaaag aaaaaaaaaa aaaaaaaaag  60
aatctaaaaa aaaaaaaaaa aaaaaaaaaa aaaaaaaaaa aaaaaaaaaa aaaaaaaaaa  120
aaaaa                                                              125

SEQ ID NO: 11            moltype = DNA  length = 130
FEATURE                  Location/Qualifiers
source                   1..130
                         mol_type = other DNA
                         organism = synthetic construct
SEQUENCE: 11
aaaaaaaaaa aaaaaaaaaa aaaaaaaaaa aaaaaaaaaa aaaaaaaaaa aaaaaaaaaa  60
gcatatgact aaaaaaaaaa aaaaaaaaaa aaaaaaaaaa aaaaaaaaaa aaaaaaaaaa  120
aaaaaaaaaa                                                         130

SEQ ID NO: 12            moltype = DNA  length = 110
FEATURE                  Location/Qualifiers
source                   1..110
                         mol_type = other DNA
                         organism = synthetic construct
SEQUENCE: 12
aaaaaaaaaa aaaaaaaaaa aaaaaaaaaa gcatatgact aaaaaaaaaa aaaaaaaaaa  60
aaaaaaaaaa aaaaaaaaaa aaaaaaaaaa aaaaaaaaaa aaaaaaaaaa             110

SEQ ID NO: 13            moltype = DNA  length = 121
FEATURE                  Location/Qualifiers
source                   1..121
                         mol_type = other DNA
                         organism = synthetic construct
SEQUENCE: 13
aaaaaaaaaa aaaaaaaaaa aaaaaaaaaa aaaaaaaaaa aaaaaaaaaa aaaaaaaaaa  60
gaaaaaaaaa aaaaaaaaaa aaaaaaaaaa aaaaaaaaaa aaaaaaaaaa aaaaaaaaaa  120
a                                                                  121

SEQ ID NO: 14            moltype = DNA  length = 126
FEATURE                  Location/Qualifiers
source                   1..126
                         mol_type = other DNA
                         organism = synthetic construct
SEQUENCE: 14
aaaaaaaaaa aaaaaaaaaa aaaaaaaaaa aaaaaaaaaa aaaaaaaaaa aaaaaaaaaa  60
atgcataaaa aaaaaaaaaa aaaaaaaaaa aaaaaaaaaa aaaaaaaaaa aaaaaaaaaa  120
aaaaaa                                                             126

SEQ ID NO: 15            moltype =   length =
SEQUENCE: 15
000

SEQ ID NO: 16            moltype =   length =
SEQUENCE: 16
000

SEQ ID NO: 17            moltype =   length =
SEQUENCE: 17
000

SEQ ID NO: 18            moltype = DNA  length = 10
FEATURE                  Location/Qualifiers
source                   1..10
                         mol_type = other DNA
                         organism = synthetic construct
SEQUENCE: 18
gcatatgact                                                         10

SEQ ID NO: 19            moltype = DNA  length = 12
FEATURE                  Location/Qualifiers
source                   1..12
                         mol_type = other DNA
```

-continued

```
                        organism = synthetic construct
SEQUENCE: 19
gatatcgtat ac                                                   12

SEQ ID NO: 20           moltype = DNA  length = 213
FEATURE                 Location/Qualifiers
source                  1..213
                        mol_type = other DNA
                        organism = synthetic construct
SEQUENCE: 20
ctcgctttct tgctgtccaa tttctattaa aggttccttt gttccctaag tccaactact  60
aaactggggg atattatgaa gggccttgag catctggatt ctgcctgctc gctttcttgc  120
tgtccaattt ctattaaagg ttcctttgtt ccctaagtcc aactactaaa ctgggggata  180
ttatgaaggg ccttgagcat ctggattctg cct                            213

SEQ ID NO: 21           moltype = DNA  length = 50
FEATURE                 Location/Qualifiers
source                  1..50
                        mol_type = other DNA
                        organism = synthetic construct
SEQUENCE: 21
acatttgctt ctgacacaac tgtgttcact agcaacctca aacagacacc          50

SEQ ID NO: 22           moltype = DNA  length = 1653
FEATURE                 Location/Qualifiers
source                  1..1653
                        mol_type = other DNA
                        organism = synthetic construct
SEQUENCE: 22
atggaagacg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgagtactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg ccagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctcaaaagc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aggactgac cggcaagttg gacgcccgca agatccgcga gattctcatt  1620
aaggccaaga agggcggaaa gatcgccgtg taa                            1653

SEQ ID NO: 23           moltype = DNA  length = 2298
FEATURE                 Location/Qualifiers
source                  1..2298
                        mol_type = other DNA
                        organism = synthetic construct
SEQUENCE: 23
atggatgcta tgaaacgggg cctgtgctgc gtgctgctcc tgtgcggcgc tgtgtttgtg  60
agccctagca tcacccagga ctgctccttc caacacagcc ccatctcctc cgacttcgct  120
gtcaaaatcc gtgagctgtc tgactacctg cttcaagatt acccagtcac cgtggcctcc  180
aacctgcagg acgaggagct ctgcgggggc ctctggcggc tggtcctggc acagcgctgg  240
atggagcggc tcaagactgt cgctgggtcc aagatgcaag gcttgctgga gcgcgtgaac  300
acggagatac actttgtcac caaatgtgcc tttcagcccc cccccagctg tcttcgcttc  360
gtccagacca acatctcccg cctcctgcag gagacctccg agcagctggt ggcgctgaag  420
ccctggatca ctcgccagaa cttctcccgg tgcctggagc tgcagtgtca gcccgactcc  480
tcaaccctgc cacccccatg gagtccccgg cccctggagg ccacagcccc gacagccccg  540
ggcggcggca gcggcgatat gcaccagaag agaaccgcca tgttccagga ccctcaggag  600
agacctagga agctgcctca cctgtgtaca gagctccaga caaccatcca cgacatcatc  660
ctggagtgcg tgtactgtaa gcagcagctg ctgagaagag aggtgtacga cttcgccttc  720
agagacctgt gcatcgtgta cagagacggc aacccttacg ccgtgtgcga taagtgtctg  780
aagttctatt ccaaaatctc cgaatatagg tacatgcacg gcgacacccc taccctgcac  840
gagtacatgc tggacctcca gcctgagacc acagacctgt actgctacga gcagctgaac  900
```

```
gacagctctg aggaagagga cgagattgac ggacctgctg gccaggccga gcctgacaga  960
gcccactaca atatcgtgac attctgttgc aaatgcgact ccacactgga caagtgcctg  1020
aagttctaca gcaagatctc tgagtacaga tactactgct actctgtgta cggcaccaca  1080
ctggagcagc agtacaacaa gcctctgtgc gacctcctga tccgctgcat caactgccag  1140
aagcctctgt gccctgagga gaagcagaga cacctggaca agaagcagcg gttccacaac  1200
atcagaggca gatggaccgg caggtgcatg tcctgctgta gatcctccag aaccagacgg  1260
gagacccagc tgcactacaa catcgtgacc ttctgctgca agtgcgactc taccctgaga  1320
ctgtgcgtgc agtctaccca cgtggacatc agaaccctgg aggacctgct gatgggcacc  1380
ctgggcatcg tgtgccctat ctgctctcag aagcctatgg ccaggttcga ggaccctacc  1440
agaagaccct acaagctgcc tgacctgtgc accgagctga acacctctct gcaagacatc  1500
gagatcacct gcgtgtactg caagaccgtg ctggagctga ccgaggtgtt cgagttcgcc  1560
ttcaaggacc tgttcgtggt gtacagagac agcatccctc acgctgcctg ccacaagtgc  1620
atcgacttct attccaggat cagggagctg cgctattact ccgactctgt gatgtacggc  1680
cccaaggcca ccctccagga catcgtgctg cacctggagc ctcagaacga gatccccgtg  1740
gacctgctgt gccacgagca gctgtctgac tctgaagagg agaacgacga gatcgacggc  1800
gtgaaccacc agcacctgcc tgccaggaga gctgaacccc agcggcatac catgctgtgt  1860
atgtgcttct actctaggat cagagagctg aggtactact ctgactctgt gtacggcgac  1920
accctggaga agctgaccaa caccggcctg tacaacctgc tgatccggtg cctgaggtgc  1980
cagaagcctc tgaaccctgc cgagaagctg agacacctga acgagaagag aagattccac  2040
aagatcgctg gccactacag aggccagtgc cactcttgct gcaacagagc cagacaggag  2100
agactccagc ggagaaggga gacccaggtg gccaggagag ccgagcctca gagacacacc  2160
atgctgtgca tgtgctgcaa gtgcgaggcc agaatcgagc tggtggtgga gagctctgcc  2220
gacgacctga gagccttcca gcagctgttc ctgtctaccc tgagcttcgt gtgcccttgg  2280
tgcgcctctc agcagtaa                                                2298
```

```
SEQ ID NO: 24          moltype = DNA  length = 2711
FEATURE                Location/Qualifiers
source                 1..2711
                       mol_type = other DNA
                       organism = synthetic construct
SEQUENCE: 24
acatttgctt ctgacacaac tgtgttcact agcaacctca aacagacacc ggatccgcca  60
ccatggatgc tatgaaacgg ggcctgtgct gcgtgctgct cctgtgcggc gctgtgtttg  120
tgagccctag catcacccag gactgctcct tccaacacag ccccatctcc tccgacttcg  180
ctgtcaaaat ccgtgagctg tctgactacc tgcttcaaga ttacccagtc accgtggcct  240
ccaacctgca ggacgaggag ctctgcgggg gcctctggcg gctggtcctg gcacagcgct  300
ggatggagcg gctcaagact gtcgctgggt ccaagatgca aggcttgctg gagcgcgtga  360
acacggagat acactttgtc accaaatgtg cctttcagcc cccccccagc tgtcttcgct  420
tcgtccagac caacatctcc cgcctcctgc aggagacctc cgagcagctg gtggcgctga  480
agccctggat cactcgccag aacttctccc ggtgcctgga gctgcagtgt cagcccgact  540
cctcaaccct gccaccccca tggagtcccc ggcccctgga ggccacagcc ccgacagccc  600
cgggcggcgg cagcggcgat atgcaccaga agagaaccgc catgttccag gaccctcagg  660
agagacctag gaagctgcct cacctgtgta cagagctcca gacaaccatc cacgacatca  720
tcctggagtg cgtgtactgt aagcagcagc tgctgagaag agaggtgtac gacttcgcct  780
tcagagacct gtgcatcgtg tacagagacg gcaaccctta cgccgtgtgc gataagtgtc  840
tgaagttcta ttccaaaatc tccgaatata ggtacatgca cggcgacacc cctaccctgc  900
acgagtacat gctggacctc cagcctgaga ccacagacct gtactgctac gagcagctga  960
acgacagctc tgaggaagag gacgagattg acggacctgc tggccaggcc gagcctgaca  1020
gagcccacta caatatcgtg acattctgtt gcaaatgcga ctccacactg gacaagtgcc  1080
tgaagttcta cagcaagatc tctgagtaca gatactactg ctactctgtg tacggcacca  1140
cactggagca gcagtacaac aagcctctgt gcgacctcct gatccgctgc atcaactgcc  1200
agaagcctct gtgccctgag gagaagcaga gacacctgga caagaagcag cggttccaca  1260
acatcagagg cagatggacc ggcaggtgca tgtcctgctg tagatcctcc agaaccagac  1320
gggagaccca gctgcactac aacatcgtga ccttctgctg caagtgcgac tctaccctga  1380
gactgtgcgt gcagtctacc cacgtggaca tcagaaccct ggaggacctg ctgatgggca  1440
ccctgggcat cgtgtgccct atctgctctc agaagcctat ggccaggttc gaggacccta  1500
ccagaagacc ctacaagctg cctgacctgt gcaccgagct gaacacctct ctgcaagaca  1560
tcgagatcac ctgcgtgtac tgcaagaccg tgctggagct gaccgaggtg ttcgagttcg  1620
ccttcaagga cctgttcgtg gtgtacagag acagcatccc tcacgctgcc tgccacaagt  1680
gcatcgactt ctattccagg atcagggagc tgcgctatta ctccgactct gtgatgtacg  1740
gccccaaggc caccctccag gacatcgtgc tgcacctgga gcctcagaac gagatccccg  1800
tggacctgct gtgccacgag cagctgtctg actctgaaga ggagaacgac gagatcgacg  1860
gcgtgaacca ccagcacctg cctgccagga gagctgaacc ccagcggcat accatgctgt  1920
gtatgtgctt ctactctagg atcagagagc tgaggtacta ctctgactct gtgtacggcg  1980
acaccctgga gaagctgacc aacaccggcc tgtacaacct gctgatccgg tgcctgaggt  2040
gccagaagcc tctgaaccct gccgagaagc tgagacacct gaacgagaag agaagattcc  2100
acaagatcgc tggccactac agaggccagt gccactcttg ctgcaacaga gccagacagg  2160
agagactcca gcggagaagg gagacccagg tggccaggag agccgagcct cagagacaca  2220
ccatgctgtg catgtgctgc aagtgcgagg ccagaatcga gctggtggtg gagagctctg  2280
ccgacgacct gagagccttc cagcagctgt tcctgtctac cctgagcttc gtgtgccctt  2340
ggtgcgcctc tcagcagtaa ggcgcgccgc tcgctttctt gctgtccaat ttctattaaa  2400
ggttcctttg ttccctaagt ccaactacta aactggggga tattatgaag ggccttgagc  2460
atctggattc tgcctgctcg ctttcttgct gtccaatttc tattaaaggt tcctttgttc  2520
cctaagtcca actactaaac tgggggatat tatgaagggc cttgagcatc tggattctgc  2580
ctgaattcaa aaaaaaaaaa aaaaaaaaaa aaaaaaaaaa aaaaaaaaaa aaaaaaaaaa  2640
aaaaaaaaga tatcaaaaaa aaaaaaaaaa aaagaaaaaa aaaaaaaaaa aaagaaaaaa  2700
aaaaaaaaaa a                                                       2711
```

```
SEQ ID NO: 25          moltype = DNA  length = 2713
```

-continued

```
FEATURE              Location/Qualifiers
source               1..2713
                     mol_type = other DNA
                     organism = synthetic construct
SEQUENCE: 25
acatttgctt ctgacacaac tgtgttcact agcaacctca aacagacacc ggatccgcca  60
ccatggatgc tatgaaacgg ggcctgtgct gcgtgctgct cctgtgcggc gctgtgtttg  120
tgagccctag catcacccag gactgctcct tccaacacag ccccatctcc tccgacttcg  180
ctgtcaaaat ccgtgagctg tctgactacc tgcttcaaga ttacccagtc accgtggcct  240
ccaacctgca ggacgaggag ctctgcgggg gcctctggcg gctggtcctg gcacagcgct  300
ggatggagcg gctcaagact gtcgctgggt ccaagatgca aggcttgctg gagcgcgtga  360
acacggagat acactttgtc accaaatgtg cctttcagcc cccccccagc tgtcttcgct  420
tcgtccagac caacatctcc cgcctcctgc aggagacctc cgagcagctg gtggcgctga  480
agccctggat cactcgccag aacttctccc ggtgcctgga gctgcagtgt cagcccgact  540
cctcaaccct gccaccccca tggagtcccc ggcccctgga ggccacagcc ccgacagccc  600
cgggcggcgg cagcggcgat atgcaccaga agagaaccgc catgttccag gaccctcagg  660
agagacctag gaagctgcct cacctgtgta cagagctcca gacaaccatc cacgacatca  720
tcctggagtg cgtgtactgt aagcagcagc tgctgagaag agaggtgtac gacttcgcct  780
tcagagacct gtgcatcgtg tacagagacg gcaaccctta cgccgtgtgc gataagtgtc  840
tgaagttcta ttccaaaatc tccgaatata ggtacatgca cggcgacacc cctaccctgc  900
acgagtacat gctggacctc cagcctgaga ccacagacct gtactgctac gagcagctga  960
acgacagctc tgaggaagag gacgagattg acggacctgc tggccaggcc gagcctgaca  1020
gagcccacta caatatcgtg acattctgtt gcaaatgcga ctccacactg gacaagtgcc  1080
tgaagttcta cagcaagatc tctgagtaca gatactactg ctactctgtg tacggcacca  1140
cactggagca gcagtacaac aagcctctgt gcgacctcct gatccgctgc atcaactgcc  1200
agaagcctct gtgccctgag gagaagcaga gacacctgga caagaagcag cggttccaca  1260
acatcagagg cagatggacc ggcaggtgca tgtcctgctg tagatcctcc agaaccagac  1320
gggagaccca gctgcactac aacatcgtga ccttctgctg caagtgcgac tctaccctga  1380
gactgtgcgt gcagtctacc cacgtggaca tcagaaccct ggaggacctg ctgatgggca  1440
ccctgggcat cgtgtgccct atctgctctc agaagcctat ggccaggttc gaggacccta  1500
ccagaagacc ctacaagctg cctgacctgt gcaccgagct gaacacctct ctgcaagaca  1560
tcgagatcac ctgcgtgtac tgcaagaccg tgctggagct gaccgaggtg ttcgagttcg  1620
ccttcaagga cctgttcgtg gtgtacagag acagcatccc tcacgctgcc tgccacaagt  1680
gcatcgactt ctattccagg atcagggagc tgcgctatta ctccgactct gtgatgtacg  1740
gccccaaggc caccctccag gacatcgtgc tgcacctgga gcctcagaac gagatccccg  1800
tggacctgct gtgccacgag cagctgtctg actctgaaga ggagaacgac gagatcgacg  1860
gcgtgaacca ccagcacctg cctgccagga gagctgaacc ccagcggcat accatgctgt  1920
gtatgtgctt ctactctagg atcagagagc tgaggtacta ctctgactct gtgtacggcg  1980
acaccctgga gaagctgacc aacaccggcc tgtacaacct gctgatccgg tgcctgaggt  2040
gccagaagcc tctgaaccct gccgagaagc tgagacacct gaacgagaag agaagattcc  2100
acaagatcgc tggccactac agaggccagt gccactcttg ctgcaacaga gccagacagg  2160
agagactcca gcggagaagg gagacccagg tggccaggag agccgagcct cagagacaca  2220
ccatgctgtg catgtgctgc aagtgcgagg ccagaatcga gctggtggtg gagagctctg  2280
ccgacgacct gagagccttc cagcagctgt tcctgtctac cctgagcttc gtgtgccctt  2340
ggtgcgcctc tcagcagtaa ggcgcgccgc tcgctttctt gctgtccaat ttctattaaa  2400
ggttcctttg ttccctaagt ccaactacta aactggggga tattatgaag ggccttgagc  2460
atctggattc tgcctgctcg ctttcttgct gtccaatttc tattaaaggt tcctttgttc  2520
cctaagtcca actactaaac tgggggatat tatgaagggc cttgagcatc tggattctgc  2580
ctgaattcaa aaaaaaaaaa aaaaaaagaa aaaaaaaaaa aaaaaaagaa aaaaaaaaaa  2640
aaaaaaagat atcaaaaaaa aaaaaaaaaa aaaaaaaaaa aaaaaaaaaa aaaaaaaaaa  2700
aaaaaaaaaa aaa                                                     2713

SEQ ID NO: 26        moltype = AA  length = 765
FEATURE              Location/Qualifiers
source               1..765
                     mol_type = protein
                     organism = synthetic construct
SEQUENCE: 26
MDAMKRGLCC VLLLCGAVFV SPSITQDCSF QHSPISSDFA VKIRELSDYL LQDYPVTVAS  60
NLQDEELCGG LWRLVLAQRW MERLKTVAGS KMQGLLERVN TEIHFVTKCA FQPPPSCLRF  120
VQTNISRLLQ ETSEQLVALK PWITRQNFSR CLELQCQPDS STLPPPWSPR PLEATAPTAP  180
GGGSGDMHQK RTAMFQDPQE RPRKLPHLCT ELQTTIHDII LECVYCKQQL LRREVYDFAF  240
RDLCIVYRDG NPYAVCDKCL KFYSKISEYR YMHGDTPTLH EYMLDLQPET TDLYCYEQLN  300
DSSEEEDEID GPAGQAEPDR AHYNIVTFCC KCDSTLDKCL KFYSKISEYR YYCYSVYGTT  360
LEQQYNKPLC DLLIRCINCQ KPLCPEEKQR HLDKKQRFHN IRGRWTGRCM SCCRSSRTRR  420
ETQLHYNIVT FCCKCDSTLR LCVQSTHVDI RTLEDLLMGT LGIVCPICSQ KPMARFEDPT  480
RRPYKLPDLC TELNTSLQDI EITCVYCKTV LELTEVFEFA FKDLFVVYRD SIPHAACHKC  540
IDFYSRIREL RYYSDSVMYG PKATLQDIVL HLEPQNEIPV DLLCHEQLSD SEEENDEIDG  600
VNHQHLPARR AEPQRHTMLC MCFYSRIREL RYYSDSVYGD TLEKLTNTGL YNLLIRCLRC  660
QKPLNPAEKL RHLNEKRRFH KIAGHYRGQC HSCCNRARQE RLQRRRETQV ARRAEPQRHT  720
MLCMCCKCEA RIELVVESSA DDLRAFQQLF LSTLSFVCPW CASQQ                 765
```

-continued

```
SEQ ID NO: 27            moltype = DNA  length = 20
FEATURE                  Location/Qualifiers
source                   1..20
                         mol_type = other DNA
                         organism = synthetic construct
SEQUENCE: 27
taatacgact cactataagg                                      20
```